(12) United States Patent
Hodgkinson et al.

(10) Patent No.: US 10,390,827 B2
(45) Date of Patent: Aug. 27, 2019

(54) MULTI-LAYER POROUS FILM MATERIAL

(71) Applicant: Covidien LP, Mansfield, MA (US)

(72) Inventors: Gerald N. Hodgkinson, Guilford, CT (US); Richard P. Stevenson, Colchester, CT (US)

(73) Assignee: Covidien LP, Mansfield, MA (US)

( * ) Notice: Subject to any disclaimer, the term of this patent is extended or adjusted under 35 U.S.C. 154(b) by 77 days.

(21) Appl. No.: 15/624,311

(22) Filed: Jun. 15, 2017

(65) Prior Publication Data

US 2017/0281328 A1 Oct. 5, 2017

Related U.S. Application Data

(63) Continuation of application No. 13/690,445, filed on Nov. 30, 2012, now Pat. No. 9,681,936.

(51) Int. Cl.
*A61B 17/072* (2006.01)
*A61F 2/00* (2006.01)
*A61B 17/115* (2006.01)

(52) U.S. Cl.
CPC ...... *A61B 17/07292* (2013.01); *A61F 2/0063* (2013.01); *A61B 17/07207* (2013.01); *A61B 17/1155* (2013.01); *A61F 2002/0072* (2013.01); *F04C 2270/0421* (2013.01)

(58) Field of Classification Search
CPC .......... A61F 2/0063; A61F 2/0077; A61F 13/00068; A61F 13/0216; A61F 13/0022; A61F 13/0223; A61F 13/00; A61F 13/00029; A61F 13/00038; A61F 13/0289; A61F 2013/00536; A61F 2013/00174; A61F 2013/0054; A61F 2002/0086; A61F 2002/0072; A61F 2002/30971; A61F 2210/0004; A61F 2220/005; A61M 1/0088; A61M 1/0023; A61B 17/07292; A61B 17/072; A61B 17/07207; A61B 17/1155
See application file for complete search history.

(56) References Cited

U.S. PATENT DOCUMENTS

| | | |
|---|---|---|
| 3,054,406 A | 9/1962 | Usher |
| 3,079,606 A | 3/1963 | Bobrov et al. |
| 3,124,136 A | 3/1964 | Usher |
| 3,490,675 A | 1/1970 | Green et al. |
| 3,499,591 A | 3/1970 | Green |
| 3,797,494 A | 3/1974 | Zaffaroni |

(Continued)

FOREIGN PATENT DOCUMENTS

| | | |
|---|---|---|
| CA | 2282761 A1 | 9/1998 |
| CA | 2 667 434 A1 | 5/2008 |

(Continued)

OTHER PUBLICATIONS

European Office Action corresponding to counterpart Int'l Appln No. EP 12 198 776.2 dated Apr. 7, 2015.

(Continued)

*Primary Examiner* — David C Eastwood
*Assistant Examiner* — Mohamed G Gabr

(57) ABSTRACT

A surgical implant includes at least two porous film layers each having a plurality of pores. The porous film layers are in a stacked configuration and are interconnected to one another at a plurality of attachment points to define at least one void between the porous film layers.

15 Claims, 5 Drawing Sheets

(56) References Cited

U.S. PATENT DOCUMENTS

| | | |
|---|---|---|
| 4,347,847 A | 9/1982 | Usher |
| 4,354,628 A | 10/1982 | Green |
| 4,429,695 A | 2/1984 | Green |
| 4,452,245 A | 6/1984 | Usher |
| 4,605,730 A | 8/1986 | Shalaby et al. |
| 4,655,221 A | 4/1987 | Devereux |
| 4,834,090 A | 5/1989 | Moore |
| 4,838,884 A | 6/1989 | Dumican et al. |
| 4,927,640 A | 5/1990 | Dahlinder et al. |
| 4,930,674 A | 6/1990 | Barak |
| 5,002,551 A | 3/1991 | Linsky et al. |
| 5,014,899 A | 5/1991 | Presty et al. |
| 5,040,715 A | 8/1991 | Green et al. |
| 5,065,929 A | 11/1991 | Schulze et al. |
| 5,112,496 A | 5/1992 | Dhawan et al. |
| 5,205,459 A | 4/1993 | Brinkerhoff et al. |
| 5,263,629 A | 11/1993 | Trumbull et al. |
| 5,281,197 A | 1/1994 | Arias et al. |
| 5,307,976 A | 5/1994 | Olson et al. |
| 5,312,023 A | 5/1994 | Green et al. |
| 5,314,471 A | 5/1994 | Brauker et al. |
| 5,318,221 A | 6/1994 | Green et al. |
| 5,326,013 A | 7/1994 | Green et al. |
| 5,332,142 A | 7/1994 | Robinson et al. |
| 5,344,454 A | 9/1994 | Clarke et al. |
| 5,392,979 A | 2/1995 | Green et al. |
| 5,397,324 A | 3/1995 | Carroll et al. |
| 5,405,072 A | 4/1995 | Zlock et al. |
| 5,425,745 A | 6/1995 | Green et al. |
| 5,441,193 A | 8/1995 | Gravener |
| 5,441,507 A | 8/1995 | Wilk |
| 5,443,198 A | 8/1995 | Viola et al. |
| 5,468,253 A | 11/1995 | Bezwada et al. |
| 5,503,638 A | 4/1996 | Cooper et al. |
| 5,542,594 A | 8/1996 | McKean et al. |
| 5,549,628 A | 8/1996 | Cooper et al. |
| 5,575,803 A | 11/1996 | Cooper et al. |
| 5,645,915 A | 7/1997 | Kranzler et al. |
| 5,653,756 A | 8/1997 | Clarke et al. |
| 5,683,809 A | 11/1997 | Freeman et al. |
| 5,690,675 A | 11/1997 | Sawyer et al. |
| 5,702,409 A | 12/1997 | Rayburn et al. |
| 5,752,965 A | 5/1998 | Francis et al. |
| 5,762,256 A | 6/1998 | Mastri et al. |
| 5,766,188 A | 6/1998 | Igaki |
| 5,769,892 A | 6/1998 | Kingwell |
| 5,782,396 A | 7/1998 | Mastri et al. |
| 5,799,857 A | 9/1998 | Robertson et al. |
| 5,810,855 A | 9/1998 | Rayburn et al. |
| 5,814,057 A | 9/1998 | Oi et al. |
| 5,833,695 A | 11/1998 | Yoon |
| 5,843,096 A | 12/1998 | Igaki et al. |
| 5,871,135 A | 2/1999 | Williamson, IV et al. |
| 5,895,412 A | 4/1999 | Tucker |
| 5,895,415 A | 4/1999 | Chow et al. |
| 5,902,312 A | 5/1999 | Frater et al. |
| 5,908,427 A | 6/1999 | McKean et al. |
| 5,915,616 A | 6/1999 | Viola et al. |
| 5,931,847 A | 8/1999 | Bittner et al. |
| 5,964,774 A | 10/1999 | McKean et al. |
| 5,997,895 A | 12/1999 | Narotam et al. |
| 6,019,791 A | 2/2000 | Wood |
| 6,030,392 A | 2/2000 | Dakov |
| 6,032,849 A | 3/2000 | Mastri et al. |
| 6,045,560 A | 4/2000 | McKean et al. |
| 6,063,097 A | 5/2000 | Oi et al. |
| 6,080,169 A | 6/2000 | Turtel |
| 6,099,551 A | 8/2000 | Gabbay |
| 6,149,667 A | 11/2000 | Hovland et al. |
| 6,155,265 A | 12/2000 | Hammerslag |
| 6,210,439 B1 | 4/2001 | Firmin et al. |
| 6,214,020 B1 | 4/2001 | Mulhauser et al. |
| 6,241,139 B1 | 6/2001 | Milliman et al. |
| 6,258,107 B1 | 7/2001 | Balazs et al. |
| 6,267,772 B1 | 7/2001 | Mulhauser et al. |
| 6,270,530 B1 | 8/2001 | Eldridge et al. |
| 6,273,897 B1 | 8/2001 | Dalessandro et al. |
| 6,280,453 B1 | 8/2001 | Kugel et al. |
| 6,299,631 B1 | 10/2001 | Shalaby |
| 6,312,457 B1 | 11/2001 | DiMatteo et al. |
| 6,312,474 B1 | 11/2001 | Francis et al. |
| 6,325,810 B1 | 12/2001 | Hamilton et al. |
| 6,330,965 B1 | 12/2001 | Milliman et al. |
| 6,436,030 B2 | 8/2002 | Rehil |
| 6,454,780 B1 | 9/2002 | Wallace |
| 6,461,368 B2 | 10/2002 | Fogarty et al. |
| 6,503,257 B2 | 1/2003 | Grant et al. |
| 6,514,283 B2 | 2/2003 | DiMatteo et al. |
| 6,517,566 B1 | 2/2003 | Hovland et al. |
| 6,551,356 B2 | 4/2003 | Rousseau |
| 6,568,398 B2 | 5/2003 | Cohen |
| 6,592,597 B2 | 7/2003 | Grant et al. |
| 6,638,285 B2 | 10/2003 | Gabbay |
| 6,652,594 B2 | 11/2003 | Francis et al. |
| 6,656,193 B2 | 12/2003 | Grant et al. |
| 6,669,735 B1 | 12/2003 | Pelissier |
| 6,677,258 B2 | 1/2004 | Carroll et al. |
| 6,685,714 B2 | 2/2004 | Rousseau |
| 6,702,828 B2 | 3/2004 | Whayne |
| 6,704,210 B1 | 3/2004 | Myers |
| 6,723,114 B2 | 4/2004 | Shalaby |
| 6,726,706 B2 | 4/2004 | Dominguez |
| 6,736,823 B2 | 5/2004 | Darois et al. |
| 6,736,854 B2 | 5/2004 | Vadurro et al. |
| 6,746,458 B1 | 6/2004 | Cloud |
| 6,773,458 B1 | 8/2004 | Brauker et al. |
| 6,790,213 B2 | 9/2004 | Cherok et al. |
| 6,896,684 B2 | 5/2005 | Monassevitch et al. |
| 6,927,315 B1 | 8/2005 | Heinecke et al. |
| 6,939,358 B2 | 9/2005 | Palacios et al. |
| 6,946,196 B2 | 9/2005 | Foss |
| 6,959,851 B2 | 11/2005 | Heinrich |
| 7,087,065 B2 | 8/2006 | Ulmsten et al. |
| 7,108,701 B2 | 9/2006 | Evens et al. |
| 7,128,748 B2 | 10/2006 | Mooradian et al. |
| 7,134,438 B2 | 11/2006 | Makower et al. |
| 7,141,055 B2 | 11/2006 | Abrams et al. |
| 7,147,138 B2 | 12/2006 | Shelton, IV |
| 7,160,299 B2 | 1/2007 | Baily |
| 7,179,268 B2 | 2/2007 | Roy et al. |
| 7,210,810 B1 | 5/2007 | Iversen et al. |
| 7,232,449 B2 | 6/2007 | Sharkawy et al. |
| 7,241,300 B2 | 7/2007 | Sharkawy et al. |
| 7,307,031 B2 | 12/2007 | Carroll et al. |
| 7,311,720 B2 | 12/2007 | Mueller et al. |
| 7,377,928 B2 | 5/2008 | Zubik et al. |
| 7,434,717 B2 | 10/2008 | Shelton, IV et al. |
| 7,438,209 B1 | 10/2008 | Hess |
| 7,547,312 B2 | 6/2009 | Bauman et al. |
| 7,559,937 B2 | 7/2009 | de la Torre et al. |
| 7,571,845 B2 | 8/2009 | Viola |
| 7,594,921 B2 | 9/2009 | Browning |
| 7,604,151 B2 | 10/2009 | Hess et al. |
| 7,665,646 B2 | 2/2010 | Prommersberger |
| 7,666,198 B2 | 2/2010 | Suyker et al. |
| 7,669,747 B2 | 3/2010 | Weisenburgh, II et al. |
| 7,717,313 B2 | 5/2010 | Criscuolo et al. |
| 7,722,642 B2 | 5/2010 | Williamson, IV et al. |
| 7,744,627 B2 | 6/2010 | Orban, III et al. |
| 7,776,060 B2 | 8/2010 | Mooradian et al. |
| 7,793,813 B2 | 9/2010 | Bettuchi |
| 7,799,026 B2 | 9/2010 | Schechter et al. |
| 7,823,592 B2 | 11/2010 | Bettuchi et al. |
| 7,824,420 B2 | 11/2010 | Eldridge et al. |
| 7,845,533 B2 | 12/2010 | Marczyk et al. |
| 7,845,536 B2 | 12/2010 | Viola et al. |
| 7,846,149 B2 | 12/2010 | Jankowski |
| 7,892,247 B2 | 2/2011 | Conston et al. |
| 7,909,224 B2 | 3/2011 | Prommersberger |
| 7,909,837 B2 | 3/2011 | Crews et al. |
| 7,938,307 B2 | 5/2011 | Bettuchi |
| 7,942,890 B2 | 5/2011 | D'Agostino et al. |
| 7,950,561 B2 | 5/2011 | Aranyi |
| 7,951,166 B2 | 5/2011 | Orban, III et al. |

(56) References Cited

U.S. PATENT DOCUMENTS

| | | |
|---|---|---|
| 7,967,179 B2 | 6/2011 | Olson et al. |
| 7,988,027 B2 | 8/2011 | Olson et al. |
| 8,011,550 B2 | 9/2011 | Aranyi et al. |
| 8,016,177 B2 | 9/2011 | Bettuchi et al. |
| 8,016,178 B2 | 9/2011 | Olson et al. |
| 8,028,883 B2 | 10/2011 | Stopek |
| 8,062,330 B2 | 11/2011 | Prommersberger et al. |
| 8,083,119 B2 | 12/2011 | Prommersberger |
| 8,123,766 B2 | 2/2012 | Bauman et al. |
| 8,123,767 B2 | 2/2012 | Bauman et al. |
| 8,127,975 B2 | 3/2012 | Olson et al. |
| 8,146,791 B2 | 4/2012 | Bettuchi et al. |
| 8,157,149 B2 | 4/2012 | Olson et al. |
| 8,157,151 B2 | 4/2012 | Ingmanson et al. |
| 8,167,895 B2 | 5/2012 | D'Agostino et al. |
| 8,178,746 B2 | 5/2012 | Hildeberg et al. |
| 8,192,460 B2 | 6/2012 | Orban, III et al. |
| 8,210,414 B2 | 7/2012 | Bettuchi et al. |
| 8,225,799 B2 | 7/2012 | Bettuchi |
| 8,225,981 B2 | 7/2012 | Criscuolo et al. |
| 8,231,043 B2 | 7/2012 | Tarinelli et al. |
| 8,235,273 B2 | 8/2012 | Olson et al. |
| 8,245,901 B2 | 8/2012 | Stopek |
| 8,256,654 B2 | 9/2012 | Bettuchi et al. |
| 8,257,391 B2 | 9/2012 | Orban, III et al. |
| 8,276,800 B2 | 10/2012 | Bettuchi |
| 8,286,849 B2 | 10/2012 | Bettuchi |
| 8,308,042 B2 | 11/2012 | Aranyi |
| 8,308,045 B2 | 11/2012 | Bettuchi et al. |
| 8,308,046 B2 | 11/2012 | Prommersberger |
| 8,312,885 B2 | 11/2012 | Bettuchi et al. |
| 8,313,014 B2 | 11/2012 | Bettuchi |
| 8,348,126 B2 | 1/2013 | Olson et al. |
| 8,348,130 B2 | 1/2013 | Shah et al. |
| 8,365,972 B2 | 2/2013 | Aranyi et al. |
| 8,371,491 B2 | 2/2013 | Huitema et al. |
| 8,371,492 B2 | 2/2013 | Aranyi et al. |
| 8,371,493 B2 | 2/2013 | Aranyi et al. |
| 8,393,514 B2 | 3/2013 | Shelton, IV et al. |
| 8,408,440 B2 | 4/2013 | Olson et al. |
| 8,413,869 B2 | 4/2013 | Heinrich |
| 8,413,871 B2 | 4/2013 | Racenet et al. |
| 8,424,742 B2 | 4/2013 | Bettuchi |
| 8,453,652 B2 | 6/2013 | Stopek |
| 8,453,904 B2 | 6/2013 | Eskaros et al. |
| 8,453,909 B2 | 6/2013 | Olson et al. |
| 8,453,910 B2 | 6/2013 | Bettuchi et al. |
| 8,464,925 B2 | 6/2013 | Hull et al. |
| 8,474,677 B2 | 7/2013 | Woodard, Jr. et al. |
| 8,479,968 B2 | 7/2013 | Hodgkinson et al. |
| 8,485,414 B2 | 7/2013 | Criscuolo et al. |
| 8,496,683 B2 | 7/2013 | Prommersberger et al. |
| 8,511,533 B2 | 8/2013 | Viola et al. |
| 8,512,402 B2 | 8/2013 | Marczyk et al. |
| 8,529,600 B2 | 9/2013 | Woodard, Jr. et al. |
| 8,540,131 B2 | 9/2013 | Swayze |
| 8,551,138 B2 | 10/2013 | Orban, III et al. |
| 8,556,918 B2 | 10/2013 | Bauman et al. |
| 8,561,873 B2 | 10/2013 | Ingmanson et al. |
| 8,584,920 B2 | 11/2013 | Hodgkinson |
| 8,590,762 B2 | 11/2013 | Hess et al. |
| 8,616,430 B2 | 12/2013 | (Prommersberger) Stopek et al. |
| 8,631,989 B2 | 1/2014 | Aranyi et al. |
| 8,646,674 B2 | 2/2014 | Schulte et al. |
| 8,668,129 B2 | 3/2014 | Olson |
| 8,684,250 B2 | 4/2014 | Bettuchi et al. |
| 8,721,703 B2 | 5/2014 | Fowler |
| 8,757,466 B2 | 6/2014 | Olson et al. |
| 8,789,737 B2 | 7/2014 | Hodgkinson et al. |
| 8,820,606 B2 | 9/2014 | Hodgkinson |
| 8,870,050 B2 | 10/2014 | Hodgkinson |
| 8,920,444 B2 | 12/2014 | Hiles et al. |
| 8,939,344 B2 | 1/2015 | Olson et al. |
| 8,967,448 B2 | 3/2015 | Carter et al. |
| 9,005,243 B2 | 4/2015 | Stopek et al. |
| 9,010,606 B2 | 4/2015 | Aranyi et al. |
| 9,010,608 B2 | 4/2015 | Casasanta, Jr. et al. |
| 9,010,609 B2 | 4/2015 | Carter et al. |
| 9,010,610 B2 | 4/2015 | Hodgkinson |
| 9,010,612 B2 | 4/2015 | Stevenson et al. |
| 9,016,543 B2 | 4/2015 | (Prommersberger) Stopek et al. |
| 9,016,544 B2 | 4/2015 | Hodgkinson et al. |
| 9,027,817 B2 | 5/2015 | Milliman et al. |
| 9,044,227 B2 | 6/2015 | Shelton, IV et al. |
| 9,055,944 B2 | 6/2015 | Hodgkinson et al. |
| 9,084,602 B2 | 7/2015 | Gleiman |
| 9,107,665 B2 | 8/2015 | Hodgkinson et al. |
| 9,107,667 B2 | 8/2015 | Hodgkinson |
| 9,113,873 B2 | 8/2015 | Marczyk et al. |
| 9,113,885 B2 | 8/2015 | Hodgkinson et al. |
| 9,113,893 B2 | 8/2015 | Sorrentino et al. |
| 9,161,753 B2 | 10/2015 | Prior |
| 9,161,757 B2 | 10/2015 | Bettuchi |
| 9,186,144 B2 | 11/2015 | Stevenson et al. |
| 9,192,378 B2 | 11/2015 | Aranyi et al. |
| 9,192,379 B2 | 11/2015 | Aranyi et al. |
| 9,192,380 B2 | 11/2015 | (Tarinelli) Racenet et al. |
| 9,192,383 B2 | 11/2015 | Milliman |
| 9,192,384 B2 | 11/2015 | Bettuchi |
| 9,198,660 B2 | 12/2015 | Hodgkinson |
| 9,198,663 B1 | 12/2015 | Marczyk et al. |
| 9,204,881 B2 | 12/2015 | Penna |
| 9,220,504 B2 | 12/2015 | Viola et al. |
| 9,226,754 B2 | 1/2016 | D'Agostino et al. |
| 9,237,892 B2 | 1/2016 | Hodgkinson |
| 9,237,893 B2 | 1/2016 | Carter et al. |
| 9,277,922 B2 | 3/2016 | Carter et al. |
| 9,295,466 B2 | 3/2016 | Hodgkinson et al. |
| 9,326,773 B2 | 5/2016 | Casasanta, Jr. et al. |
| 9,345,479 B2 | 5/2016 | (Tarinelli) Racenet et al. |
| 9,351,729 B2 | 5/2016 | Orban, III et al. |
| 9,351,731 B2 | 5/2016 | Carter et al. |
| 9,351,732 B2 | 5/2016 | Hodgkinson |
| 9,364,229 B2 | 6/2016 | D'Agostino et al. |
| 9,364,234 B2 | 6/2016 | (Prommersberger) Stopek et al. |
| 9,433,412 B2 | 9/2016 | Bettuchi et al. |
| 9,433,413 B2 | 9/2016 | Stopek |
| 9,629,626 B2 | 4/2017 | Soltz et al. |
| 9,681,936 B2 | 6/2017 | Hodgkinson et al. |
| 9,931,116 B2 | 4/2018 | Racenet et al. |
| 10,022,125 B2 | 7/2018 | (Prommersberger) Stopek et al. |
| 2002/0028243 A1 | 3/2002 | Masters |
| 2002/0091397 A1 | 7/2002 | Chen |
| 2002/0151911 A1 | 10/2002 | Gabbay |
| 2002/0165559 A1 | 11/2002 | Grant et al. |
| 2002/0165563 A1 | 11/2002 | Grant et al. |
| 2003/0065345 A1 | 4/2003 | Weadock |
| 2003/0083676 A1 | 5/2003 | Wallace |
| 2003/0120284 A1 | 6/2003 | Palacios et al. |
| 2003/0181927 A1 | 9/2003 | Wallace |
| 2003/0183671 A1 | 10/2003 | Mooradian et al. |
| 2003/0196668 A1 | 10/2003 | Harrison et al. |
| 2003/0208231 A1 | 11/2003 | Williamson et al. |
| 2004/0107006 A1 | 6/2004 | Francis et al. |
| 2004/0254590 A1 | 12/2004 | Hoffman et al. |
| 2004/0260315 A1 | 12/2004 | Dell et al. |
| 2005/0002981 A1 | 1/2005 | Lahtinen et al. |
| 2005/0021085 A1 | 1/2005 | Abrams et al. |
| 2005/0059996 A1 | 3/2005 | Bauman et al. |
| 2005/0059997 A1 | 3/2005 | Bauman et al. |
| 2005/0070929 A1 | 3/2005 | Dalessandro et al. |
| 2005/0118435 A1 | 6/2005 | DeLucia et al. |
| 2005/0143756 A1 | 6/2005 | Jankowski |
| 2005/0149073 A1 | 7/2005 | Arani et al. |
| 2005/0228446 A1 | 10/2005 | Mooradian et al. |
| 2005/0283256 A1 | 12/2005 | Sommerich et al. |
| 2006/0004407 A1 | 1/2006 | Hiles et al. |
| 2006/0085030 A1 | 4/2006 | Bettuchi et al. |
| 2006/0135992 A1 | 6/2006 | Bettuchi et al. |
| 2006/0141012 A1 | 6/2006 | Gingras |
| 2006/0173470 A1 | 8/2006 | Oray et al. |
| 2006/0178683 A1 | 8/2006 | Shimoji et al. |
| 2006/0271104 A1 | 11/2006 | Viola et al. |
| 2007/0026031 A1 | 2/2007 | Bauman et al. |

(56) References Cited

U.S. PATENT DOCUMENTS

| | | |
|---|---|---|
| 2007/0034669 A1 | 2/2007 | de la Torre et al. |
| 2007/0049953 A2 | 3/2007 | Shimoji et al. |
| 2007/0060863 A1 | 3/2007 | Goeken et al. |
| 2007/0123839 A1 | 5/2007 | Rousseau et al. |
| 2007/0179528 A1 | 8/2007 | Soltz et al. |
| 2007/0203509 A1 | 8/2007 | Bettuchi |
| 2007/0203510 A1 | 8/2007 | Bettuchi |
| 2007/0207186 A1 | 9/2007 | Scanlon et al. |
| 2007/0243227 A1 | 10/2007 | Gertner |
| 2007/0246505 A1 | 10/2007 | Pace-Floridia et al. |
| 2008/0009811 A1 | 1/2008 | Cantor |
| 2008/0029570 A1 | 2/2008 | Shelton et al. |
| 2008/0082126 A1 | 4/2008 | Murray et al. |
| 2008/0110959 A1 | 5/2008 | Orban et al. |
| 2008/0125812 A1 | 5/2008 | Zubik et al. |
| 2008/0140115 A1 | 6/2008 | Stopek |
| 2008/0161831 A1 | 7/2008 | Bauman et al. |
| 2008/0161832 A1 | 7/2008 | Bauman et al. |
| 2008/0169327 A1 | 7/2008 | Shelton et al. |
| 2008/0169328 A1 | 7/2008 | Shelton |
| 2008/0169329 A1 | 7/2008 | Shelton et al. |
| 2008/0169330 A1 | 7/2008 | Shelton et al. |
| 2008/0169331 A1 | 7/2008 | Shelton et al. |
| 2008/0169332 A1 | 7/2008 | Shelton et al. |
| 2008/0169333 A1 | 7/2008 | Shelton et al. |
| 2008/0200949 A1 | 8/2008 | Hiles et al. |
| 2008/0216855 A1 | 9/2008 | Nasca |
| 2008/0220047 A1 | 9/2008 | Sawhney et al. |
| 2008/0230583 A1 | 9/2008 | Heinrich |
| 2008/0290134 A1 | 11/2008 | Bettuchi et al. |
| 2008/0308608 A1 | 12/2008 | Prommersberger |
| 2008/0314960 A1 | 12/2008 | Marczyk et al. |
| 2009/0001121 A1 | 1/2009 | Hess et al. |
| 2009/0001122 A1 | 1/2009 | Prommersberger et al. |
| 2009/0001123 A1 | 1/2009 | Morgan et al. |
| 2009/0001124 A1 | 1/2009 | Hess et al. |
| 2009/0001125 A1 | 1/2009 | Hess et al. |
| 2009/0001126 A1 | 1/2009 | Hess et al. |
| 2009/0001128 A1 | 1/2009 | Weisenburgh, II et al. |
| 2009/0001130 A1 | 1/2009 | Hess et al. |
| 2009/0005808 A1 | 1/2009 | Hess et al. |
| 2009/0030452 A1 | 1/2009 | Bauman et al. |
| 2009/0043334 A1 | 2/2009 | Bauman et al. |
| 2009/0069893 A1 | 3/2009 | Paukshto et al. |
| 2009/0076510 A1 | 3/2009 | Bell et al. |
| 2009/0076528 A1 | 3/2009 | Sgro |
| 2009/0078739 A1 | 3/2009 | Viola |
| 2009/0095791 A1 | 4/2009 | Eskaros et al. |
| 2009/0095792 A1 | 4/2009 | Bettuchi |
| 2009/0120994 A1 | 5/2009 | Murray et al. |
| 2009/0134200 A1 | 5/2009 | Tarinelli et al. |
| 2009/0206125 A1 | 8/2009 | Huitema et al. |
| 2009/0206126 A1 | 8/2009 | Huitema et al. |
| 2009/0206139 A1 | 8/2009 | Hall et al. |
| 2009/0206141 A1 | 8/2009 | Huitema et al. |
| 2009/0206142 A1 | 8/2009 | Huitema et al. |
| 2009/0206143 A1 | 8/2009 | Huitema et al. |
| 2009/0218384 A1 | 9/2009 | Aranyi |
| 2009/0227969 A1 | 9/2009 | Jaeb et al. |
| 2009/0277944 A9 | 11/2009 | Dalessandro et al. |
| 2009/0277947 A1 | 11/2009 | Viola |
| 2009/0287230 A1 | 11/2009 | D'Agostino et al. |
| 2009/0299450 A1 | 12/2009 | Johnson et al. |
| 2010/0012704 A1 | 1/2010 | Tarinelli Racenet et al. |
| 2010/0065606 A1 | 3/2010 | Stopek |
| 2010/0065607 A1 | 3/2010 | Orban, III et al. |
| 2010/0072254 A1 | 3/2010 | Aranyi et al. |
| 2010/0087767 A1 | 4/2010 | McNeil |
| 2010/0147921 A1 | 6/2010 | Olson |
| 2010/0147922 A1 | 6/2010 | Olson |
| 2010/0147923 A1* | 6/2010 | D'Agostino ......... A61B 17/072 227/179.1 |
| 2010/0203155 A1* | 8/2010 | Wei ................ A61F 2/30 424/549 |
| 2010/0243707 A1 | 9/2010 | Olson et al. |
| 2010/0243708 A1 | 9/2010 | Aranyi |
| 2010/0243711 A1 | 9/2010 | Olson et al. |
| 2010/0249805 A1 | 9/2010 | Olson et al. |
| 2010/0264195 A1 | 10/2010 | Bettuchi |
| 2010/0282815 A1 | 11/2010 | Bettuchi et al. |
| 2010/0331880 A1 | 12/2010 | Stopek |
| 2011/0024476 A1 | 2/2011 | Bettuchi et al. |
| 2011/0024481 A1 | 2/2011 | Bettuchi et al. |
| 2011/0036894 A1 | 2/2011 | Bettuchi |
| 2011/0042442 A1 | 2/2011 | Viola et al. |
| 2011/0046650 A1 | 2/2011 | Bettuchi |
| 2011/0057016 A1 | 3/2011 | Bettuchi |
| 2011/0087279 A1 | 4/2011 | Shah et al. |
| 2011/0166673 A1* | 7/2011 | Patel ................ A61L 27/3633 623/23.72 |
| 2011/0215132 A1 | 9/2011 | Aranyi et al. |
| 2011/0224631 A1 | 9/2011 | Simmons et al. |
| 2012/0074199 A1 | 3/2012 | Olson et al. |
| 2012/0080336 A1 | 4/2012 | Shelton, IV et al. |
| 2012/0083723 A1 | 4/2012 | Vitaris et al. |
| 2012/0145767 A1 | 6/2012 | Shah et al. |
| 2012/0187179 A1 | 7/2012 | Gleiman |
| 2012/0197272 A1 | 8/2012 | Oray et al. |
| 2012/0241499 A1 | 9/2012 | Baxter, III et al. |
| 2012/0273547 A1 | 11/2012 | Hodgkinson et al. |
| 2013/0037596 A1 | 2/2013 | Bear et al. |
| 2013/0053798 A1 | 2/2013 | Coulthard et al. |
| 2013/0105548 A1 | 5/2013 | Hodgkinson et al. |
| 2013/0105553 A1 | 5/2013 | (Tarinelli) Racenet et al. |
| 2013/0112732 A1 | 5/2013 | Aranyi et al. |
| 2013/0112733 A1 | 5/2013 | Aranyi et al. |
| 2013/0146641 A1 | 6/2013 | Shelton, IV et al. |
| 2013/0153633 A1 | 6/2013 | Casasanta, Jr. et al. |
| 2013/0153634 A1 | 6/2013 | Carter et al. |
| 2013/0153635 A1 | 6/2013 | Hodgkinson |
| 2013/0153636 A1 | 6/2013 | Shelton, IV et al. |
| 2013/0153638 A1 | 6/2013 | Carter et al. |
| 2013/0153639 A1 | 6/2013 | Hodgkinson et al. |
| 2013/0153640 A1 | 6/2013 | Hodgkinson |
| 2013/0153641 A1 | 6/2013 | Shelton, IV et al. |
| 2013/0161374 A1 | 6/2013 | Swayze |
| 2013/0181031 A1 | 7/2013 | Colson et al. |
| 2013/0193186 A1 | 8/2013 | (Tarinelli) Racenet et al. |
| 2013/0193190 A1 | 8/2013 | Carter et al. |
| 2013/0193191 A1 | 8/2013 | Stevenson et al. |
| 2013/0193192 A1 | 8/2013 | Casasanta, Jr. et al. |
| 2013/0209659 A1 | 8/2013 | Racenet et al. |
| 2013/0211540 A1* | 8/2013 | Tate ................ A61B 17/56 623/23.57 |
| 2013/0221062 A1 | 8/2013 | Hodgkinson |
| 2013/0240600 A1 | 9/2013 | Bettuchi |
| 2013/0240601 A1 | 9/2013 | Bettuchi et al. |
| 2013/0240602 A1 | 9/2013 | Stopek |
| 2013/0256380 A1 | 10/2013 | Schmid et al. |
| 2013/0277411 A1 | 10/2013 | Hodgkinson et al. |
| 2013/0306707 A1 | 11/2013 | Viola et al. |
| 2013/0310873 A1 | 11/2013 | Stopek (nee Prommersberger) et al. |
| 2013/0327807 A1 | 12/2013 | Olson et al. |
| 2014/0012317 A1 | 1/2014 | Orban et al. |
| 2014/0021242 A1 | 1/2014 | Hodgkinson et al. |
| 2014/0027490 A1 | 1/2014 | Marczyk et al. |
| 2014/0034704 A1 | 2/2014 | Ingmanson et al. |
| 2014/0048580 A1 | 2/2014 | Merchant et al. |
| 2014/0061280 A1 | 3/2014 | Ingmanson et al. |
| 2014/0061281 A1 | 3/2014 | Hodgkinson |
| 2014/0084042 A1 | 3/2014 | (Prommersberger) Stopek et al. |
| 2014/0097224 A1 | 4/2014 | Prior |
| 2014/0117066 A1 | 5/2014 | Aranyi et al. |
| 2014/0130330 A1 | 5/2014 | Olson et al. |
| 2014/0131418 A1 | 5/2014 | Kostrzewski |
| 2014/0131419 A1 | 5/2014 | Bettuchi |
| 2014/0138423 A1 | 5/2014 | Whitfield et al. |
| 2014/0151431 A1 | 6/2014 | Hodgkinson et al. |
| 2014/0155916 A1 | 6/2014 | Hodgkinson et al. |
| 2014/0158742 A1 | 6/2014 | Stopek (nee Prommersberger) et al. |
| 2014/0166721 A1 | 6/2014 | Stevenson et al. |
| 2014/0197224 A1 | 7/2014 | Penna |

(56) References Cited

U.S. PATENT DOCUMENTS

| | | |
|---|---|---|
| 2014/0203061 A1 | 7/2014 | Hodgkinson |
| 2014/0217147 A1 | 8/2014 | Milliman |
| 2014/0217148 A1 | 8/2014 | Penna |
| 2014/0239046 A1 | 8/2014 | Milliman |
| 2014/0239047 A1 | 8/2014 | Hodgkinson et al. |
| 2014/0252062 A1 | 9/2014 | Mozdzierz |
| 2015/0001276 A1 | 1/2015 | Hodgkinson et al. |
| 2015/0041347 A1 | 2/2015 | Hodgkinson |
| 2015/0097018 A1 | 4/2015 | Hodgkinson |
| 2015/0115015 A1 | 4/2015 | Prescott et al. |
| 2015/0122872 A1 | 5/2015 | Olson et al. |
| 2015/0164503 A1 | 6/2015 | Stevenson et al. |
| 2015/0164506 A1 | 6/2015 | Carter et al. |
| 2015/0164507 A1 | 6/2015 | Carter et al. |
| 2015/0196297 A1 | 7/2015 | (Prommersberger) Stopek et al. |
| 2015/0209033 A1 | 7/2015 | Hodgkinson |
| 2015/0209045 A1 | 7/2015 | Hodgkinson et al. |
| 2015/0209048 A1 | 7/2015 | Carter et al. |
| 2015/0231409 A1 | 8/2015 | Racenet et al. |
| 2015/0305743 A1 | 10/2015 | Casasanta et al. |
| 2015/0327864 A1 | 11/2015 | Hodgkinson et al. |
| 2016/0022268 A1 | 1/2016 | Prior |
| 2016/0045200 A1 | 2/2016 | Milliman |
| 2016/0058451 A1 | 3/2016 | (Tarinelli) Racenet et al. |
| 2016/0100834 A1 | 4/2016 | Viola et al. |
| 2016/0106430 A1 | 4/2016 | Carter et al. |
| 2016/0113647 A1 | 4/2016 | Hodgkinson |
| 2016/0157857 A1 | 6/2016 | Hodgkinson et al. |
| 2016/0174988 A1 | 6/2016 | D'Agostino et al. |
| 2016/0367253 A1 | 12/2016 | Hodgkinson |
| 2018/0125491 A1 | 5/2018 | Aranyi |
| 2018/0140301 A1 | 5/2018 | Milliman |
| 2018/0168654 A1 | 6/2018 | Hodgkinson et al. |
| 2018/0214147 A1 | 8/2018 | Merchant et al. |

FOREIGN PATENT DOCUMENTS

| | | | |
|---|---|---|---|
| CN | 101310680 A | | 11/2008 |
| CN | 101332110 A | | 12/2008 |
| DE | 1 99 24 311 A1 | | 11/2000 |
| EP | 0327022 A2 | | 8/1989 |
| EP | 0594148 A1 | | 4/1994 |
| EP | 0667119 A1 | | 8/1995 |
| EP | 1064883 A1 | | 1/2001 |
| EP | 1256317 A2 | | 11/2002 |
| EP | 1256318 A1 | | 11/2002 |
| EP | 1520525 A1 | | 4/2005 |
| EP | 1621141 A2 | | 2/2006 |
| EP | 1702570 A1 | | 9/2006 |
| EP | 1759640 A2 | | 3/2007 |
| EP | 1815804 A1 | | 8/2007 |
| EP | 1825820 A1 | | 8/2007 |
| EP | 1929958 A2 | | 6/2008 |
| EP | 1994890 A1 | | 11/2008 |
| EP | 2005894 A2 | | 12/2008 |
| EP | 2005895 A2 | | 12/2008 |
| EP | 2008595 A2 | | 12/2008 |
| EP | 2039308 A2 | | 3/2009 |
| EP | 2090231 A1 | | 8/2009 |
| EP | 2090244 A2 | | 8/2009 |
| EP | 2090252 A2 | | 8/2009 |
| EP | 2163211 A2 | | 3/2010 |
| EP | 2189121 A1 | | 5/2010 |
| EP | 2198787 A1 | | 6/2010 |
| EP | 2236098 A2 | | 10/2010 |
| EP | 2236099 A1 | | 10/2010 |
| EP | 2258282 A2 | | 12/2010 |
| EP | 2292276 A2 | | 3/2011 |
| EP | 2311386 A2 | | 4/2011 |
| EP | 2436348 A1 | | 4/2012 |
| EP | 2462880 A2 | | 6/2012 |
| EP | 2497431 A1 | | 9/2012 |
| EP | 2517637 A1 | | 10/2012 |
| EP | 2586380 A1 | | 5/2013 |
| EP | 2604195 A1 | | 6/2013 |
| EP | 2604197 A2 | | 6/2013 |
| EP | 2620105 A1 | | 7/2013 |
| EP | 2620106 A2 | | 7/2013 |
| EP | 2630922 A1 | | 8/2013 |
| EP | 2644125 A2 | | 10/2013 |
| EP | 2762091 A2 | | 8/2014 |
| JP | 2000166933 A | | 6/2000 |
| JP | 2002202213 A | | 7/2002 |
| JP | 2007124166 A | | 5/2007 |
| JP | 2008510515 A | | 4/2008 |
| JP | 2009525109 A | | 7/2009 |
| JP | 2009538245 A | | 11/2009 |
| JP | 2012100912 A | | 5/2012 |
| WO | 9005489 A1 | | 5/1990 |
| WO | 9516221 A1 | | 6/1995 |
| WO | 9622055 A1 | | 7/1996 |
| WO | 9701989 A1 | | 1/1997 |
| WO | 9713463 A1 | | 4/1997 |
| WO | 9817180 A1 | | 4/1998 |
| WO | 9838923 A1 | | 9/1998 |
| WO | 9945849 A1 | | 9/1999 |
| WO | 03082126 A1 | | 10/2003 |
| WO | 03088845 A2 | | 10/2003 |
| WO | 03094743 A1 | | 11/2003 |
| WO | 03105698 A2 | | 12/2003 |
| WO | 2005079675 A2 | | 9/2005 |
| WO | 2006023578 A2 | | 3/2006 |
| WO | 2006044490 A2 | | 4/2006 |
| WO | 2006083748 A1 | | 8/2006 |
| WO | 2007088402 A2 | | 8/2007 |
| WO | 2007121579 A1 | | 11/2007 |
| WO | 2007140262 A2 | | 12/2007 |
| WO | 2008057281 A2 | | 5/2008 |
| WO | 2008109125 A1 | | 9/2008 |
| WO | 2010075298 A2 | | 7/2010 |
| WO | 2011143183 A2 | | 11/2011 |
| WO | 2012044848 A1 | | 4/2012 |
| WO | 2012135593 A1 | | 10/2012 |

OTHER PUBLICATIONS

European Office Action corresponding to counterpart Int'l Appln No. EP 13 156 297.7 dated Apr. 10, 2015.

Australian Examination Report No. 1 corresponding to counterpart Int'l Appln No. AU 2011250822 dated May 18, 2015.

European Office Action corresponding to counterpart Int'l Appln No. EP 12 186 175.1 dated Jun. 1, 2015.

Chinese Office Action corresponding to counterpart Int'l Appln No. CN 201010517292.8 dated Jun. 2, 2015.

Extended European Search Report corresponding to counterpart Int'l Appln No. EP 14 17 4814.5 dated Jun. 9, 2015.

Australian Examination Report No. 1 corresponding to counterpart Int'l Appln No. AU 2014200584 dated Jun. 15, 2015.

European Office Action corresponding to counterpart Int'l Appln No. EP 13 180 881.8 dated Jun. 19, 2015.

European Office Action corresponding to counterpart Int'l Appln No. EP 14 157 195.0 dated Jul. 2, 2015.

Extended European Search Report corresponding to counterpart Int'l Appln No. EP 12 19 6902.6 dated Aug. 6, 2015.

Extended European Search Report corresponding to counterpart Int'l Appln No. EP 14 15 2060.1 dated Aug. 14, 2015.

Chinese Office Action corresponding to counterpart Int'l Appln No. CN 201210129787.2 dated Aug. 24, 2015.

Chinese Notification of Reexamination corresponding to counterpart Int'l Appln. No. CN 201010517292.8 dated Jun. 2, 2015.

Japanese Office Action corresponding to counterpart Int'l Appln. No. JP 2014-216989 dated Sep. 11, 2015.

Canadian First Office Action corresponding to counterpart Int'l Appln. No. CA 2,686,105 dated Sep. 17, 2015.

Japanese Office Action corresponding to counterpart Int'l Appln. No. JP 2012-040188 dated Oct. 21, 2015.

European Communication corresponding to counterpart Int'l Appln. No. EP 13 17 6895.4 dated Nov. 5, 2015.

Chinese First Office Action corresponding to counterpart Int'l Appln. No. CN 201210544552 dated Nov. 23, 2015.

(56) References Cited

OTHER PUBLICATIONS

Chinese First Office Action corresponding to counterpart Int'l Appln. No. CN 201210545228 dated Nov. 30, 2015.
Extended European Search Report corresponding to counterpart Int'l Appln. No. EP 15 18 0491.1 dated Dec. 9, 2015.
Extended European Search Report corresponding to counterpart Int'l Appln. No. EP 15 18 3819.0 dated Dec. 11, 2015.
Canadian Office Action corresponding to counterpart Int'l Appln. No. CA 2,697,819 dated Jan. 6, 2016.
Canadian Office Action corresponding to counterpart Int'l Appln. No. CA 2,696,419 dated Jan. 14, 2016.
European Office Action corresponding to counterpart Int'l Appln. No. EP 12 19 8776.2 dated Jan. 19, 2016.
Extended European Search Report corresponding to counterpart Int'l Appln. No. EP 15 17 4146.9 dated Jan. 20, 2016.
Chinese First Office Action corresponding to counterpart Int'l Appln. No. CN 201310353628.5 dated Jan. 25, 2016.
Extended European Search Report corresponding to counterpart Int'l Appln. No. EP 12 19 6912.5 dated Feb. 1, 2016.
Japanese Office Action corresponding to counterpart Int'l Appln. No. JP 2012-098903 dated Feb. 22, 2016.
Extended European Search Report corresponding to counterpart Int'l Appln. No. EP 12 19 8753.1 dated Feb. 24, 2016.
Chinese First Office Action corresponding to counterpart Int'l Appln. No. CN 201410449019A dated Mar. 30, 2016.
Extended European Search Report corresponding to counterpart Int'l Appln. No. EP 16 15 0232.3 dated Apr. 12, 2016.
European Office Action corresponding to counterpart Int'l Appln. No. EP 11 18 3256.4 dated Apr. 20, 2016.
Australian Examination Report No. 1 corresponding to counterpart Int'l Appln. No. AU 2012244169 dated May 10, 2016.
European Office Action corresponding to counterpart Int'l Appln. No. EP 10 25 0715.9 dated May 12, 2016.
Chinese First Office Action corresponding to counterpart Int'l Appln. No. CN 201410778512.0 dated May 13, 2016.
Australian Examination Report No. 1 corresponding to counterpart Int'l Appln. No. AU 2012227358 dated May 16, 2016.
Japanese Office Action corresponding to counterpart Int'l Appln. No. JP 2012-040188 dated May 17, 2016.
Australian Examination Report No. 1 corresponding to counterpart Int'l Appln. No. AU 2012244380 dated May 20, 2016.
Australian Examination Report No. 1 corresponding to counterpart Int'l Appln. No. AU 2014227480 dated May 21, 2016.
Australian Examination Report No. 1 corresponding to counterpart Int'l Appln. No. AU 2012254977 dated May 30, 2016.
Extended European Search Report corresponding to counterpart Int'l Appln. No. EP 16 15 3647.9 dated Jun. 3, 2016.
Extended European Search Report corresponding to EP No. 12 19 1035.0, completed Jan. 11, 2013 and dated Jan. 18, 2013; 7 pages.
Extended European Search Report corresponding to EP No. 12 18 6175.1, completed Jan. 15, 2013 and dated Jan. 23, 2013; 7 pages.
Extended European Search Report corresponding to EP No. 12 19 1114.3, completed Jan. 23, 2013 and dated Jan. 31, 2013; 10 pages.
Extended European Search Report corresponding to EP No. 12 19 2224.9, completed Mar. 14, 2013 and dated Mar. 26, 2013; 8 pages.
Extended European Search Report corresponding to EP No. 12 19 6911.7, completed Apr. 18, 2013 and dated Apr. 24, 2013; 8 pages.
Extended European Search Report corresponding to EP 12 19 1035.0, completed Jan. 11, 2013 and dated Jan. 18, 2013; 7 pages.
Extended European Search Report corresponding to EP 12 19 6904.2, completed Mar. 28, 2013 and dated Jul. 26, 2013; 8 pages.
Extended European Search Report corresponding to EP 12 19 8749.9 completed May 21, 2013 and dated May 31, 2013; 8 pages.
Japanese Office Action dated Aug. 17, 2017, issued in JP Appln. No. 2013229471.
Chinese First Office Action corresponding to Patent Application CN 201410588811.8 dated Dec. 5, 2017.
European Office Action corresponding to Patent Application EP 16 16 6367.9 dated Dec. 11, 2017.
Chinese First Office Action corresponding to Patent Application CN 201610279682.3 dated Jan. 10, 2018.
Japanese Office Action corresponding to Patent Application JP 2013-154561 dated Jan. 15, 2018.
Australian Examination Report No. 1 corresponding to Patent Application AU 2017225037 dated Jan. 23, 2018.
Canadian Office Action corresponding to Patent Application CA 2,790,743 dated May 14, 2018.
European Office Action corresponding to Patent Application EP 14 15 7195.0 dated Jun. 12, 2018.
Japanese Office Action dated May 1, 2018 in JP Appln. No. 2013229471.
Australian Office Action dated Oct. 24, 2017, issued in AU Appln. No. 2013234420.
Cai, W., Gupta, R. B. and Updated by Staff 2012. Hydrogels. Kirk-Othmer Encyclopedia of Chemical Technology. 1-20.
Extended European Search Report corresponding to EP 13 17 7437.4, completed Sep. 11, 2013 and dated Sep. 19, 2013; (6 pp).
Extended European Search Report corresponding to EP 13 17 7441.6, completed Sep. 11, 2013 and dated Sep. 19, 2013; (6 pp).
Extended European Search Report corresponding to EP 07 86 1534.1, completed Sep. 20, 2013 and dated Sep. 30, 2013; (5 pp).
Extended European Search Report corresponding to EP 13 18 3876.5, completed Oct. 14, 2013 and dated Oct. 24, 2013; (5 pp).
Extended European Search Report corresponding to EP 13 17 1856.1, completed Oct. 29, 2013 and dated Nov. 7, 2013; (8 pp).
Extended European Search Report corresponding to EP 13 18 0373.6, completed Oct. 31, 2013 and dated Nov. 13, 2013; (7 pp).
Extended European Search Report corresponding to EP 13 18 0881.8, completed Nov. 5, 2013 and dated Nov. 14, 2013; (6 pp).
Extended European Search Report corresponding to EP 13 17 6895.4, completed Nov. 29, 2013 and dated Dec. 12, 2013; (5 pp).
Extended European Search Report corresponding to EP 13 18 2911.1, completed Dec. 2, 2013 and dated Dec. 16, 2013 (8 pp).
Extended European Search Report corresponding to EP 10 25 1795.0, completed Dec. 11, 2013 and dated Dec. 20, 2013; (6 pp).
Extended European Search Report corresponding to EP 13 18 7911.6, completed Jan. 22, 2014 and dated Jan. 31, 2014; (8 pp).
International Search Report corresponding to European Application No. EP 05 02 2585.3, completed on Jan. 25, 2006 and dated Feb. 3, 2006; 4 pages.
International Search Report corresponding to European Application No. EP 06 00 4598, completed on Jun. 22, 2006; 2 pages.
International Search Report corresponding to European Application No. EP 06 01 6962.0, completed on Jan. 3, 2007 and dated Jan. 11, 2007; 10 pages.
International Search Report corresponding to International Application No. PCT/US05/36740, completed on Feb. 20, 2007 and dated Mar. 23, 2007; 8 pages.
International Search Report corresponding to International Application No. PCT/US20071022713, completed on Apr. 21, 2008 and dated May 15, 2008; 1 page.
International Search Report corresponding to International Application No. PCT/US2008/002981, completed on Jun. 9, 2008 and dated Jun. 26, 2008; 2 pages.
International Search Report corresponding to European Application No. EP 08 25 1779, completed on Jul. 14, 2008 and dated Jun. 23, 2008; 5 pages.
International Search Report corresponding to European Application No. EP 08 25 1989.3, completed on Mar. 11, 2010 and dated Mar. 24, 2010; 6 pages.
International Search Report corresponding to European Application No. EP 10 25 0639.1, completed on Jun. 17, 2010 and dated Jun. 28, 2010; 7 pages.
International Search Report corresponding to European Application No. EP 10 25 0715.9, completed on Jun. 30, 2010 and dated Jul. 20, 2010; 3 pages.
International Search Report corresponding to European Application No. EP 05 80 4382.9, completed on Oct. 5, 2010 and dated Oct. 12, 2010; 3 pages.
International Search Report corresponding to European Application No. EP 10 25 1437.9, completed on Nov. 22, 2010 and dated Dec. 16, 2010; 3 pages.

(56) References Cited

OTHER PUBLICATIONS

International Search Report corresponding to European Application No. EP 09 25 28975, completed on Feb. 7, 2011 and dated Feb. 15, 2011; 3 pages.
International Search Report corresponding to European Application No. EP 10 25 06425, completed on Mar. 25, 2011 and dated Apr. 4, 2011; 4 pages.
International Search Report corresponding to European Application No. EP 11 18 8309.6, completed on Dec. 15, 2011 and dated Jan. 12, 2012; 3 pages.
International Search Report corresponding to European Application No. EP 12 15 2229.6, completed on Feb. 23, 2012 and dated Mar. 1, 2012; 4 pages.
International Search Report corresponding to European Application No. EP 12 15 05119.9, completed on Apr. 16, 2012 and dated Apr. 24, 2012; 7 pages.
International Search Report corresponding to European Application No. EP 12 15 2541.4, completed on Apr. 23, 2012 and dated May 3, 2012; 10 pages.
International Search Report corresponding to European Application No. EP 12 16 5609.4, completed on Jul. 5, 2012 and dated Jul. 12, 2012; 8 pages.
International Search Report corresponding to European Application No. EP 12 15 8861.0, completed on Jul. 17, 2012 and dated Jul. 24, 2012; 9 pages.
International Search Report corresponding to European Application No. EP 12 16 5878.5, completed on Jul. 24, 2012 and dated Aug. 6, 2012; 8 pages.
Extended European Search Report corresponding to EP 14 18 1127.3, completed Oct. 16, 2014 and dated Nov. 10, 2014; (7 pp).
Extended European Search Report corresponding to EP 08 72 6500.5, completed Feb. 20, 2014 and dated Mar. 3, 2014; (7 pp).
Extended European Search Report corresponding to EP 13 19 5919.9, completed Feb. 10, 2014 and dated Mar. 3, 2014; (7 pp).
Extended European Search Report corresponding to EP 13 19 2123.1, completed Jan. 30, 2014 and dated Feb. 10, 2014; (8 pp).
Extended European Search Report corresponding to EP 13 19 6816.6, completed Mar. 28, 2014 and dated Apr. 9, 2014; (9 pp).
Extended European Search Report corresponding to EP 13 19 5019.8, completed Mar. 14, 2014 and dated Mar. 24, 2014; (7 pp).
Extended European Search Report corresponding to EP 13 19 2111.6, completed Feb. 13, 2014 and dated Feb. 27, 2014; (10 pp).
Extended European Search Report corresponding to EP 13 19 7958.5, completed Apr. 4, 2014 and dated Apr. 15, 2014; (8 pp).
Extended European Search Report corresponding to EP 14 15 6342.9, completed Jul. 22, 2014 and dated Jul. 29, 2014 (8 pp).
Extended European Search Report corresponding to EP 14 15 7195.0, completed Jun. 5, 2014 and dated Jun. 18, 2014; (9 pp).
Extended European Search Report corresponding to EP 14 16 9739.1, completed Aug. 19, 2014 and dated Aug. 29, 2014; (7 pp).
Extended European Search Report corresponding to EP 14 15 7997.9, completed Sep. 9, 2014 and dated Sep. 17, 2014; (8 pp).
Extended European Search Report corresponding to EP 14 16 8904.2, completed Sep. 10, 2014 and dated Sep. 18, 2014; (8 pp).
Extended European Search Report corresponding to EP 13 19 4995.0, completed Jun. 5, 2014 and dated Oct. 13, 2014; (10 pp).
Extended European Search Report corresponding to EP 13 15 4571.7, completed Oct. 10, 2014 and dated Oct. 20, 2014; (8 pp).
Extended European Search Report corresponding to EP 14 18 1125.7, completed Oct. 16, 2014 and dated Oct. 24, 2014; (7 pp).
Extended European Search Report corresponding to EP 14 19 0419.3, completed Mar. 24, 2015 and dated Mar. 30, 2015; (6 pp).
Extended European Search Report corresponding to EP 07 00 5842.5, complete May 13, 2013 and dated May 29, 2013; 7 pages.
Extended European Search Report corresponding to EP 12 19 8776.2, completed May 16, 2013 and dated May 27, 2013; 8 pages.
Extended European Search Report corresponding to EP 13 15 6297.7 completed Jun. 4, 2013 and dated Jun. 13, 2013; 7 pages.
Extended European Search Report corresponding to EP 13 17 3985.6, completed Aug. 19, 2013 and dated Aug. 28, 2013; 6 pages.
Extended European Search Report corresponding to EP 13 17 3986.4, completed Aug. 20, 2013 and dated Aug. 29, 2013; 7 pages.
European Office Action corresponding to counterpart Int'l Appln. No. EP 14 17 2681.0 dated May 13, 2016.
Chinese Office Action corresponding to counterpart Int'l Appln. No. CN 201210545228 dated Jun. 29, 2016.
Japanese Office Action corresponding to counterpart Int'l Appln. No. JP 2012-250058 dated Jun. 29, 2016.
European Office Action corresponding to counterpart Int'l Appln. No. EP 14 15 7997.9 dated Jun. 29, 2016.
Canadian Office Action corresponding to counterpart Int'l Appln. No. CA 2,712,617 dated Jun. 30, 2016.
Chinese First Office Action corresponding to counterpart Int'l Appln. No. CN 2013103036903 dated Jun. 30, 2016.
Australian Patent Examination Report No. 1 corresponding to counterpart Int'l Appln. No. AU 2012250278 dated Jul. 10, 2016.
Australian Patent Examination Report No. 1 corresponding to counterpart Int'l Appln. No. AU 2012244382 dated Jul. 10, 2016.
Japanese Office Action corresponding to counterpart Int'l Appln. No. JP 2012-255242 dated Jul. 26, 2016.
Japanese Office Action corresponding to counterpart Int'l Appln. No. JP 2012-268668 dated Jul. 27, 2016.
European Office Action corresponding to counterpart Int'l Appln. No. EP 14 15 2060A dated Aug. 4, 2016.
European Office Action corresponding to counterpart Int'l Appln. No. EP 12 16 5609.4 dated Aug. 5, 2016.
European Office Action corresponding to counterpart Int'l Appln. No. Ep 15 15 2392.5 dated Aug. 8, 2016.
Japanese Office Action corresponding to counterpart Int'l Appln. No. JP 2013-003624 dated Aug. 25, 2016.
Australian Patent Examination Report No. 1 corresponding to counterpart Int'l Appln. No. AU 2012261752 dated Sep. 6, 2016.
Japanese Office Action corresponding to counterpart Int'l Appln. No. JP 2014-252703 dated Sep. 26, 2016.
European Office Action corresponding to counterpart Int'l Appln. No. EP 12 19 8776.2 dated Sep. 12, 2016.
Japanese Office Action corresponding to counterpart Int'l Appln. No. JP 2013-000321 dated Sep. 13, 2016.
Chinese Second Office Action corresponding to counterpart Int'l Appln. No. CN 201310353628.5 dated Sep. 26, 2016.
European Office Action corresponding to counterpart Int'l Appln. No. EP 12 15 2541.4 dated Sep. 27, 2016.
Australian Patent Examination Report No. 1 corresponding to counterpart Int'l Appln. No. AU 2012268923 dated Sep. 28, 2016.
Extended European Search Report corresponding to EP 13 19 4995.0, completed Jun. 5, 2014 and dated Jun. 16, 2014; (5 pp).

* cited by examiner

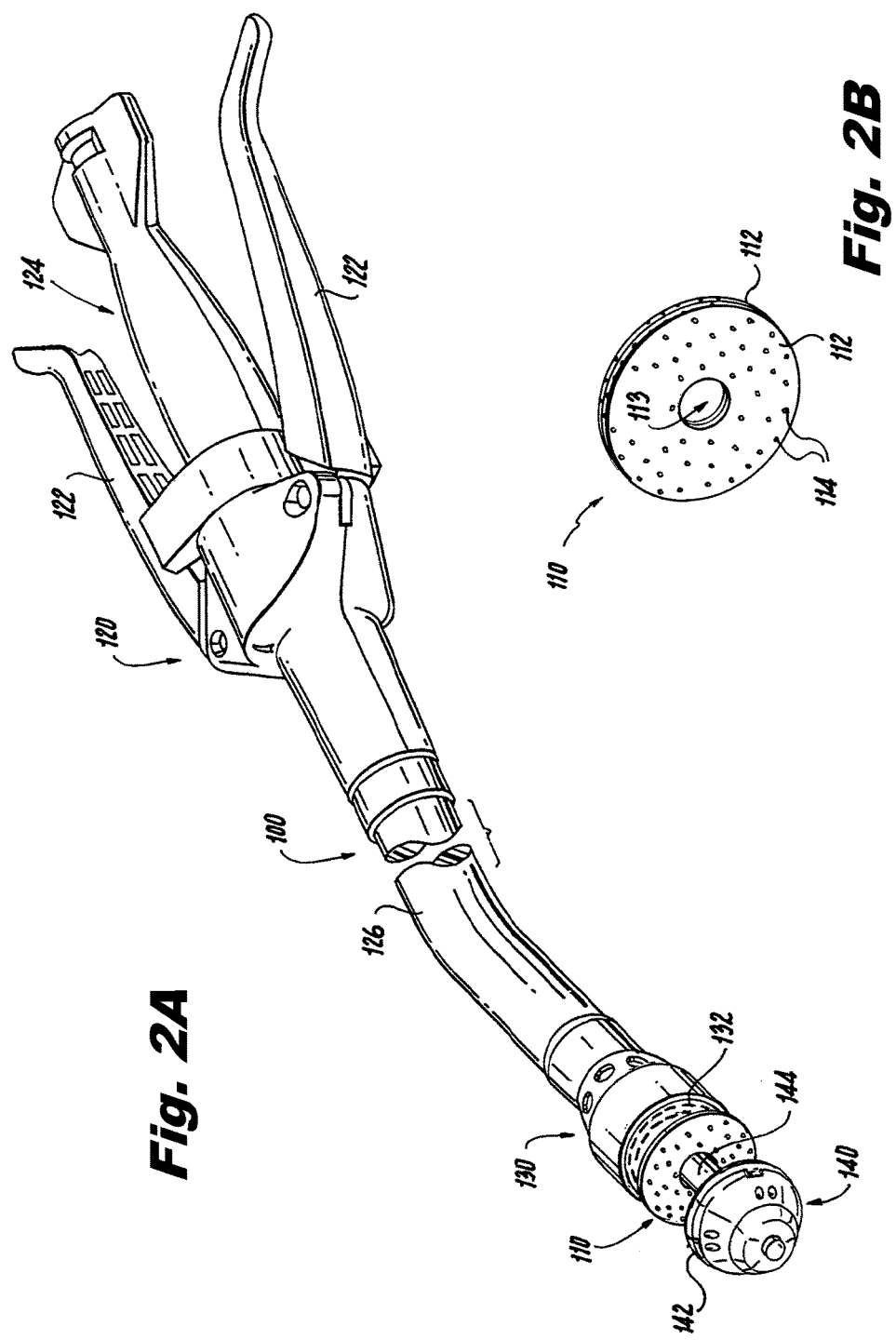

MULTI-LAYER POROUS FILM MATERIAL

CROSS-REFERENCE TO RELATED APPLICATIONS

The present application is a continuation application which claims the benefit of and priority to U.S. patent application Ser. No. 13/690,445, filed on Nov. 30, 2012, the entire disclosure of which is hereby incorporated by reference herein.

BACKGROUND

1. Technical Field

The present disclosure relates to medical devices, and more particularly, to multi-layered porous films for use as surgical implants.

2. Background of Related Art

The use of medical devices, and more specifically, implants, is known. Surgical implants include, for example, meshes for hernia repair, buttresses for staple line reinforcement, patches and sealants for repair of tissue defects and hemostasis, scaffolds for tissue integration, and other wound closure and tissue repair devices. The performance requirements of each of these implants are different, and thus, the material and construction of these implants vary and are specific to the surgical procedure being performed.

It would be advantageous to provide a surgical implant that can be used in a variety of surgical applications, wherein the properties of each layer of the implant can be controlled by material selection, pore size, and pore distribution, and the layered construction of the implant can be tailored to produce an implant having the desired mechanical strength and tissue compatibility necessary for favorable host interaction.

SUMMARY

A surgical implant of the present disclosure includes at least two porous substrates each having a plurality of openings. The porous substrates are in a stacked configuration and are interconnected to one another at a plurality of attachment points to define at least one void between the porous substrates.

According to an aspect of the present disclosure, a surgical implant includes a first porous film layer including a plurality of pores layered on top of a second porous film layer including a plurality of pores. The first and second porous film layers are interconnected to one another at a plurality of attachment points that define at least one void within the surgical implant between the first and second porous film layers. In embodiments, the attachment points are substantially evenly spaced about the surgical implant.

The first and second porous film layers may be fabricated from a biodegradable, a non-degradable material, or combinations thereof. In embodiments, the first and second porous film layers are substantially planar. In other embodiments, the first and second porous film layers may be non-planar and shaped to conform to a specific tissue surface. The first and second porous film layers may have the same or a different thickness, the same or a different elasticity modulus, and/or the same or a different degree of porosity. In embodiments, the first and second porous film layers may be uniaxially oriented in the same or different directions.

The surgical implant may include an adhesion barrier layer and/or an adhesion layer applied to an outer surface of the first and/or second porous film layers. The adhesion barrier layer and adhesion layer may be provided as films. The surgical implant may also include a filler material disposed within the openings of the first porous layer, the openings of the second porous film layer, and/or the voids between the first and second porous film layers. In embodiments, the filler material is a drug. In some embodiments, the filler material is a hydrogel.

The surgical implant may include a third porous film layer including a plurality of pores. The third porous film layer is interposed between the first and second porous film layers, and is interconnected by at least one attachment point with at least one of the first and second porous film layers.

BRIEF DESCRIPTION OF THE DRAWINGS

The foregoing objects and advantages of the disclosure will become more apparent from the reading of the following description in connection with the accompanying drawings, in which:

FIG. 2A is a perspective view of an embodiment of a surgical implant of the present disclosure for use with a circular surgical stapling device;

FIG. 2B is a front, perspective view of the surgical implant of FIG. 2A;

DETAILED DESCRIPTION

The present disclosure is directed to a multi-layered implant including at least two porous film layers joined at attachment points for use in a variety of surgical applications. The porous nature of the films and the multi-layered construction of the implant provide spaces for fluid transfer and filling, tissue ingrowth, and loading of filler materials, such as drug or biologic factors.

The following discussion includes a description of the presently disclosed surgical implant and exemplary embodiments of construction and use in accordance with the principles of the present disclosure. The presently disclosed surgical implants may be any medical device, such as scaffolds, grafts, patches, slings, pledgets, growth matrices, drug delivery devices, wound plugs, and, in general, soft tissue repair devices and surgical prostheses. It should be understood that the device may also be utilized as topically applied medical products, such as wound dressings, coverings, and the like, that can be used in medical/surgical procedures.

Figure 1A:
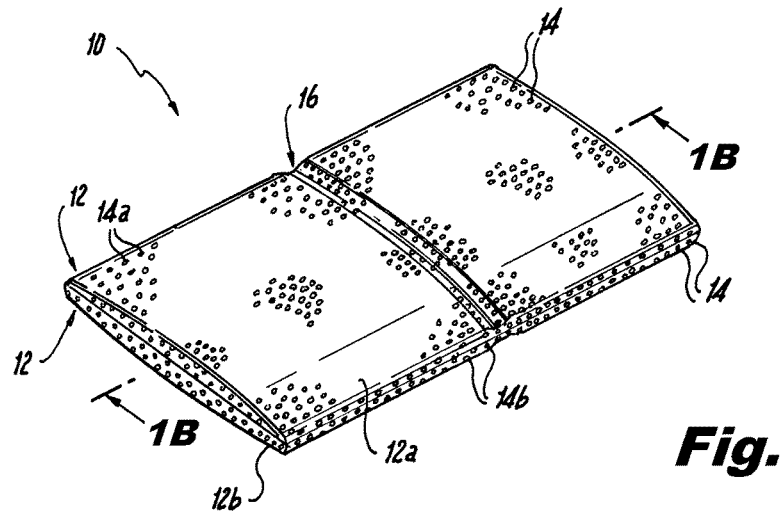
FIGS. 1A and 1B are perspective and cross-sectional views, respectively, of a surgical implant in accordance with an embodiment of the present disclosure.
Figure 1B:
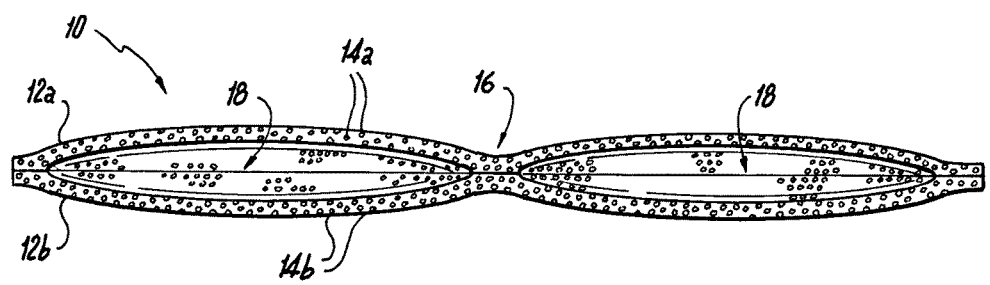

Referring now to the figures, wherein like components are designated by like reference numerals throughout the several views, FIGS. 1A and 1B illustrate a surgical implant 10 including at least two porous substrates 12 overlying one another, e.g., first porous film layer 12a and second porous film layer 12b. Each of the porous substrates 12 includes openings 14, illustrated as openings 14a and 14b, respectively, such as pores, voids, or holes over at least a portion of a surface thereof. The porous film layers 12a and 12b may be formed by any suitable process, such as cast extrusion, molding, co-extrusion, or blown film processes. While the surgical implant 10 of the present disclosure is formed solely from porous film layers, it is envisioned that a surgical implant of the present disclosure may also include a porous substrate in the form of a foam or fibrous layer.

The porous substrates are fabricated from any biodegradable and/or non-degradable material. The term "biodegradable" as used herein is defined to include both bioabsorbable and bioresorbable materials. By biodegradable, it is meant that the material decomposes, or loses structural integrity under body conditions (e.g., enzymatic degradation or hydrolysis), or is broken down (physically or chemically) under physiologic conditions in the body, such that the degradation products are excretable or absorbable by the body. Absorbable materials are absorbed by biological tissues and disappear in vivo at the end of a given period, which can vary, for example, from hours to several months, depending on the chemical nature of the material. It should be understood that such materials include natural, synthetic, bioabsorbable, and/or certain non-absorbable materials, as well as combinations thereof.

Representative natural biodegradable polymers which may be used to form a porous substrate include: polysaccharides such as alginate, dextran, chitin, chitosan, hyaluronic acid, cellulose, collagen, gelatin, fucans, glycosaminoglycans, and chemical derivatives thereof (substitutions and/or additions of chemical groups including, for example, alkyl, alkylene, amine, sulfate, hydroxylations, carboxylations, oxidations, and other modifications routinely made by those skilled in the art); catgut; silk; linen; cotton; and proteins such as albumin, casein, zein, silk, and soybean protein; and combinations such as copolymers and blends thereof, alone or in combination with synthetic polymers.

Synthetically modified natural polymers which may be used to form a porous substrate include cellulose derivatives such as alkyl celluloses, hydroxyalkyl celluloses, cellulose ethers, cellulose esters, nitrocelluloses, and chitosan. Examples of suitable cellulose derivatives include methyl cellulose, ethyl cellulose, hydroxypropyl cellulose, hydroxypropyl methyl cellulose, hydroxybutyl methyl cellulose, cellulose acetate, cellulose propionate, cellulose acetate butyrate, cellulose acetate phthalate, carboxymethyl cellulose, cellulose triacetate, cellulose sulfate sodium salt, and combinations thereof.

Representative synthetic biodegradable polymers which may be utilized to form a porous substrate include polyhydroxy acids prepared from lactone monomers (such as glycolide, lactide, caprolactone, ε-caprolactone, valerolactone, and δ-valerolactone), carbonates (e.g., trimethylene carbonate, tetramethylene carbonate, and the like), dioxanones (e.g., 1,4-dioxanone and p-dioxanone), 1,dioxepanones (e.g., 1,4-dioxepan-2-one and 1,5-dioxepan-2-one), and combinations thereof. Polymers formed therefrom include: polylactides; poly(lactic acid); polyglycolides; poly(glycolic acid); poly(trimethylene carbonate); poly(dioxanone); poly(hydroxybutyric acid); poly(hydroxyvaleric acid); poly(lactide-co-(ε-caprolactone-)); poly(glycolide-co-(ε-caprolactone)); polycarbonates; poly(pseudo amino acids); poly(amino acids); poly(hydroxyalkanoate)s such as polyhydroxybutyrate, polyhydroxyvalerate, poly(3-hydroxybutyrate-co-3-hydroxyvalerate), polyhydroxyoctanoate, and polyhydroxyhexanoate; polyalkylene oxalates; polyoxaesters; polyanhydrides; polyester anyhydrides; poly-ortho esters; and copolymers, block copolymers, homopolymers, blends, and combinations thereof.

Some non-limiting examples of suitable non-degradable materials from which a porous substrate may be made include: polyolefins such as polyethylene (including ultra high molecular weight polyethylene) and polypropylene including atactic, isotactic, syndiotactic, and blends thereof; polyethylene glycols; polyethylene oxides; polyisobutylene and ethylene-alpha olefin copolymers; fluorinated polyolefins such as fluoroethylenes, fluoropropylenes, fluoroPEGSs, and polytetrafluoroethylene; polyamides such as nylon, Nylon 6, Nylon 6,6, Nylon 6,10, Nylon 11, Nylon 12, and polycaprolactam; polyamines; polyimines; polyesters such as polyethylene terephthalate, polyethylene naphthalate, polytrimethylene terephthalate, and polybutylene terephthalate; polyethers; polybutester; polytetramethylene ether glycol; 1,4-butanediol; polyurethanes; acrylic polymers; methacrylics; vinyl halide polymers such as polyvinyl chloride; polyvinyl alcohols; polyvinyl ethers such as polyvinyl methyl ether; polyvinylidene halides such as polyvinylidene fluoride and polyvinylidene chloride; polychlorofluoroethylene; polyacrylonitrile; polyaryletherketones; polyvinyl ketones; polyvinyl aromatics such as polystyrene; polyvinyl esters such as polyvinyl acetate; etheylene-methyl methacrylate copolymers; acrylonitrile-styrene copolymers; ABS resins; ethylene-vinyl acetate copolymers; alkyd resins; polycarbonates; polyoxymethylenes; polyphosphazine; polyimides; epoxy resins; aramids; rayon; rayon-triacetate; spandex; silicones; and copolymers and combinations thereof.

A porous substrate of a surgical implant of the present disclosure may be provided in a variety of shapes and sizes to accommodate a variety of defects and tissue fascia that may need repair. Generally, a porous substrate is substantially planar and configured as a sheet that may be arranged in a layered or stacked configuration. A porous substrate, however, may, in embodiments, include non-planar surfaces that are sized and shaped to conform to a tissue surface. A porous substrate can be produced at a desired size and shape, or may be cut to a suitable size and shape for the envisaged application of use. A porous substrate may be provided in a variety of thicknesses depending upon the properties desired, e.g., stiffness and strength. In embodiments, a porous substrate (individual layer) may be from about 25 μm to about 500 µm thick, in some embodiments, from about 40 µm to about 250 µm thick, and in other embodiments, from about 50 µm to about 100 µm thick.

The openings in a porous substrate of a surgical implant of the present disclosure may be present as a surface characteristic or a bulk material property, which partially or completely penetrates the porous substrate, and may be uniformly or randomly distributed across portions thereof. In some embodiments, the openings do not extend across the entire thickness of a porous substrate, but rather are present at a portion of the surface thereof. Those skilled in the art reading the present disclosure may envision a variety of distribution patterns and configurations of the openings in a porous substrate. It is envisioned that the porous substrate may, in embodiments, be partially or substantially non-porous.

The porous substrate may be rendered porous by any number of processes, including, for example, die rolling; laser micro-perforating; solvent leaching of salt, sugar, or starch crystals; among other mechanical, electrical, and chemical processes within the purview of those skilled in the art. The openings of the porous substrate may be sized and configured to permit fibroblast through-growth and ordered collagen laydown, resulting in integration of the surgical implant into the body. In embodiments, the openings may be from about 50 micrometers to about 500 micrometers in diameter, in some embodiments, from about 100 micrometers to about 400 micrometers in diameter, and in yet other embodiments, from about 200 micrometers to about 300 micrometers in diameter. In embodiments, the openings may cover from about 20% to about 80% of the area of a porous substrate, in some embodiments, from about 30% to about 70% of the area, in yet other embodiments, from about 40% to about 60% of the area of a porous substrate. It should be understood that different thicknesses, weights, and porosities of a porous substrate may be selected by varying material selection and manufacturing conditions.

Referring again to FIGS. 1A and 1B, first and second porous film layers 12a and 12b are joined at spaced attachment points 16 to create voids or pockets 18 between the first and second porous film layers 12a and 12b. The first and second porous film layers 12a and 12b may be joined by a number of bonding processes, including ultrasonic welding and adhesive bonding, among other bonding techniques within the purview of those skilled in the art. In embodiments, the attachment points 16 are of substantially similar size and/or shape and may be positioned at substantially evenly spaced intervals across first and second porous film layers 12a and 12b, forming a plurality of voids 18 between the first and second porous film layers 12a and 12b. In some embodiments, the attachment points 16 may be provided around the entire periphery of the implant 10, forming a single, large void 18 between the first and second porous film layers 12a and 12b. In other embodiments, the size, shape, and/or position of the attachment points 16 may vary.

Figure 1C:
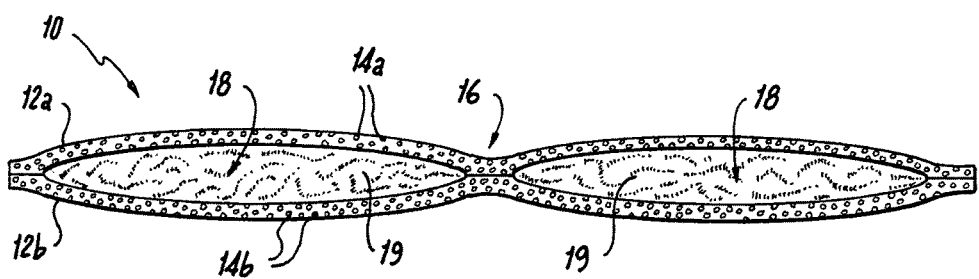
FIG. 1C is a cross-sectional view of the surgical implant of FIGS. 1A and 1B including a filler material in accordance with another embodiment of the present disclosure.

In embodiments, as illustrated in FIG. 1C, the openings 14 and/or voids 18 may be loaded with filler material(s) 19, such as drugs or biologic factors, among other secondary materials such as foams, hydrogels, adhesives, sealants, salts, sugars, etc. In embodiments, the filler material 19 may fill about 5% to about 100% of the openings 14 and/or voids 18 of the surgical implant 10, in some embodiments, from about 10% to about 80% of the openings 14 and/or voids 18, and in yet other embodiments, from about 25% to about 75% of the openings 14 and/or voids 18. The filler material 19 may be incorporated into the surgical implant 10 during fabrication, or after the surgical implant 10 is formed. The implant or medical device can have spaced, intermittent attachment points that are circular, linear, or have any shape. The attachment points can form separate pockets in the implant or medical device, or render the implant or medical device with a quilt-like configuration.

In embodiments, filler material 19 may include hydrogels which may be used as a means to absorb blood and as carriers of thrombogenic agents for blood clotting and hemostasis at wound sites. Hydrogels can be modified with any number of conjugated molecules such as cell adhesion proteins, growth factors, peptides, and endogenous growth factor capturing molecules, such as heparin sulfate, to promote tissue ingrowth and healing. In embodiments, the filler material 19 may include releasable factors that have an associated binding interaction that will release agents by unbinding and diffusion, or filler material degradation.

Examples of filler materials 19 which may be utilized in accordance with the present disclosure for example, include: anti-adhesives; antimicrobials; analgesics; antipyretics; anesthetics; antiepileptics; antihistamines; anti-inflammatories; cardiovascular drugs; diagnostic agents; sympathomimetics; cholinomimetics; antimuscarinics; antispasmodics; hormones; growth factors; muscle relaxants; adrenergic neuron blockers; antineoplastics; immunogenic agents; immunosuppressants; gastrointestinal drugs; diuretics; steroids; lipids; lipopolysaccharides; polysaccharides; platelet activating drugs; clotting factors; cancer treating chemical agents; and enzymes. It is also intended that combinations of filler materials may be used.

Other filler materials 19 include: local anesthetics; non-steroidal antifertility agents; parasympathomimetic agents; psychotherapeutic agents; tranquilizers; decongestants; sedative hypnotics; steroids; sulfonamides; sympathomimetic agents; vaccines; vitamins; antimalarials; anti-migraine agents; anti-parkinson agents such as L-dopa; anti-spasmodics; anticholinergic agents (e.g., oxybutynin); antitussives; bronchodilators; cardiovascular agents, such as coronary vasodilators and nitroglycerin; alkaloids; analgesics; narcotics such as codeine, dihydrocodeinone, meperidine, morphine and the like; non-narcotics, such as salicylates, aspirin, acetaminophen, d-propoxyphene and the like; opioid receptor antagonists, such as naltrexone and naloxone; anti-cancer agents; anti-convulsants; anti-emetics; antihistamines; anti-inflammatory agents, such as hormonal agents, hydrocortisone, prednisolone, prednisone, non-hormonal agents, allopurinol, indomethacin, phenylbutazone and the like; prostaglandins; cytotoxic drugs; chemotherapeutics, estrogens; antibacterials; antibiotics; anti-fungals; anti-virals; anticoagulants; anticonvulsants; antidepressants; antihistamines; and immunological agents.

Examples of yet other suitable filler materials 19 include: viruses and cells; peptides, polypeptides and proteins, as well as analogs, muteins, and active fragments thereof; immunoglobulins; antibodies; cytokines (e.g., lymphokines, monokines, chemokines); blood clotting factors; hemopoietic factors; interleukins (IL-2, IL-3, IL-4, IL-6); interferons (β-IFN, α-IFN and γ-IFN); erythropoietin; nucleases; tumor necrosis factor; colony stimulating factors (e.g., GCSF, GM-CSF, MCSF); insulin; anti-tumor agents and tumor suppressors; blood proteins such as fibrin, thrombin, fibrinogen, synthetic thrombin, synthetic fibrin, synthetic fibrinogen; gonadotropins (e.g., FSH, LH, CG, etc.); hormones and hormone analogs (e.g., growth hormone); vaccines (e.g., tumoral, bacterial and viral antigens); somatostatin; antigens; blood coagulation factors; growth factors (e.g., bone or nerve growth factor, insulin-like growth factor); bone morphogenic proteins; TGF-B; protein inhibitors; protein antagonists; protein agonists; nucleic acids, such as antisense molecules, DNA, RNA, RNAi; oligonucleotides; polynucleotides; and ribozymes. It is contemplated that the filler material can be released over time. The filler material may be released or degrade over time or may be non-degradable.

Exemplary embodiments of construction and use of the present surgical implants are provided below. While embodiments are illustrated and described with respect to specific surgical applications, it should be understood that the surgical implants may be used in any of a variety of surgical procedures, and that elements and features illustrate or described in connection with one exemplary embodiment may be combined with elements and features of another exemplary embodiment.

Surgical implants of the present disclosure may be utilized in surgical stapling procedures. As illustrated in FIGS. 2A and 2B, there is disclosed an exemplary surgical stapling apparatus or surgical stapler 100 (i.e., a circular stapler) for use in stapling tissue and applying a surgical implant, or surgical buttress 110, of the present disclosure to tissue. Surgical stapling apparatus 100 generally includes a handle assembly 120 having at least one pivotable actuating handle member 122, and an advancing member 124. Extending from handle member 120, there is provided a tubular body portion 126 which may be constructed so as to have a curved shape along its length. Body portion 126 terminates in a staple cartridge assembly 130 which includes an annular array of staple retaining slots 132 having a staple (not shown) disposed in each one of staple retaining slots 132. Positioned distally of staple cartridge assembly 130 there is provided an anvil assembly 140 including an anvil member 142 and a shaft 144 operatively associated therewith for removably connecting anvil assembly 140 to a distal end portion of stapling apparatus 100.

Reference may be made to commonly owned U.S. Pat. No. 5,915,616 to Viola et al., entitled "Surgical Fastener Applying Apparatus," the entire contents of which is incorporated herein by reference, for a detailed discussion of the construction and operation of an annular stapling device.

A surgical buttress 110, in accordance with the present disclosure, is positioned about the shaft 144 of the anvil assembly 140. Surgical buttress 110 includes porous layers 112 each having openings 114 disposed through at least a portion thereof, and a central aperture 113 for positioning the surgical buttress 110 about the shaft 144 of the anvil assembly 140. It should be understood that while the surgical buttress 110 is shown as being associated with the anvil assembly 140, the surgical buttress 110 may, alternatively or additionally, be associated with staple cartridge assembly 130. Surgical buttress 110 may be configured into any shape, size, or dimension suitable to fit any surgical stapling, fastening, or firing apparatus Surgical buttress 110 is provided to reinforce and seal staple lines applied to tissue by surgical stapling apparatus 100. The openings 114 and/or voids (not shown, similar to voids 18) of the surgical buttress 110 promote tissue ingrowth, and may fill with blood thereby improving clot integration into the surgical buttress 110. The relatively thin construction of the porous film layers 112 renders the surgical buttress 110 flexible and more easily penetrated by staples and a stapler knife blade. As described above, the openings 114 and/or voids (not shown) of the surgical buttress 110 may be loaded with filler material(s).

Figure 3:
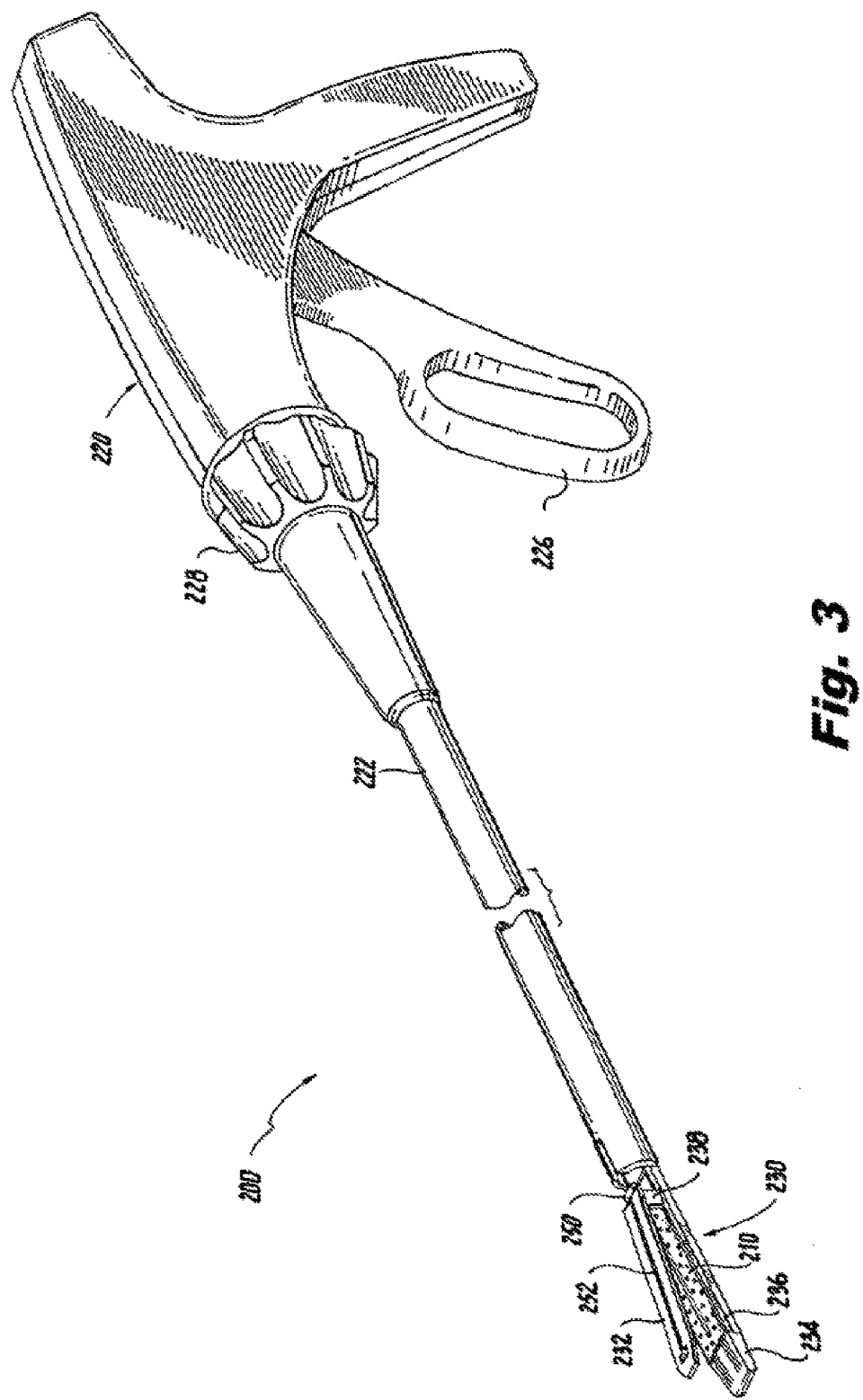
FIG. 3 is a perspective view of an embodiment of a surgical implant and a linear surgical stapling apparatus in accordance with another embodiment of the present disclosure.

FIG. 3 illustrates another exemplary surgical stapling apparatus or surgical stapler 200 (i.e., a linear stapler) for use in stapling tissue and applying a surgical buttress 210 to the tissue. Surgical stapling apparatus 200 generally includes a handle 220 having an elongate tubular member 222 extending distally therefrom. A jaw assembly 230 is mounted on a distal end 224 of elongate tubular member 222. Jaw assembly 230 includes a staple clinching anvil jaw member 232 and a receiving jaw member 234 configured to receive a staple cartridge assembly 236. Jaw assembly 230 may be permanently affixed to elongate tubular member 222 or may be detachable and thus replaceable with a new jaw assembly 230. Staple clinching anvil jaw member 232 is movably mounted on distal end 238 of jaw assembly 230 and is movable between an open position spaced apart from staple cartridge jaw member 234 to a closed position substantially adjacent staple cartridge jaw member 234. A surgical buttress 210 is releasably attached to the staple cartridge assembly 234 and/or the anvil jaw member 232.

Surgical stapling apparatus 200 further includes a trigger 226 movably mounted on handle 220. Actuation of trigger 226 initially operates to move anvil jaw member 232 from the open to the closed position relative to staple cartridge jaw member 234 and subsequently actuates surgical stapling apparatus 200 to apply lines of staples to tissue. In order to properly orient jaw assembly 230 relative to the tissue to be stapled, surgical stapling apparatus 200 is additionally provided with a rotation knob 228 mounted on handle 220. Rotation of rotation knob 228 relative to handle 220 rotates elongate tubular member 222 and jaw assembly 230 relative to handle 220 so as to properly orient jaw assembly 230 relative to the tissue to be stapled.

A driver 250 is provided to move anvil jaw member 232 between the open and closed positions relative to staple cartridge jaw member 234. Driver 250 moves between a longitudinal slot 252 formed in anvil jaw member 232. A knife (not shown) is associated with driver 250 to cut tissue captured between anvil jaw member 232 and staple cartridge jaw member 234 as driver 250 passes through slot 252.

Reference may be made to commonly owned U.S. Pat. Nos. 6,330,965 and 6,241,139, each to Milliman et al. and entitled "Surgical Stapling Apparatus," the entire contents of each of which is incorporated herein by reference, for a detailed discussion of the construction and operation of a linear stapling device.

Figure 4:
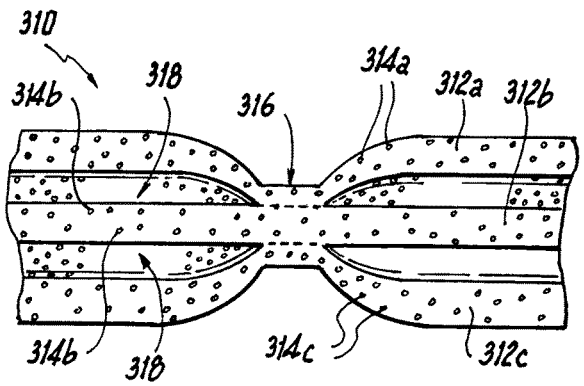
FIG. 4 is a partial, cross-sectional view of a surgical implant in accordance with a further embodiment of the present disclosure.

Surgical implants in accordance with the present disclosure may also be utilized to repair tissue defects, such as hernia repair procedures. As illustrated in FIG. 4, a hernia repair device 310 includes a first porous film layer 312a, a second porous film layer 312b, and a third porous film layer 312c, each overlying one another. Each porous film layer 312a-312c includes openings 314a-314c, respectively. The second porous film layer 312b is sandwiched, or interposed, between the first and third porous film layers 312a and 312c. The first, second, and third porous film layers 312a-312c are joined at attachment points 316 and define voids 318 between the successive layers. In embodiments, the second porous film layer 312b may be fabricated from a material having a higher modulus of elasticity than the first and third porous film layers 312a and 312c to create a stiffer material that may act as a reinforcing layer to the surgical implant 310, and minimize or prevent implant shrinkage that may occur with the use of fibrous hernia repair devices. The first and third porous film layers 312a and 312c may be fabricated from a more flexible material that is more pliant than the second porous film layer 312b to reduce tissue abrasion and increase patient comfort.

Figure 5A:
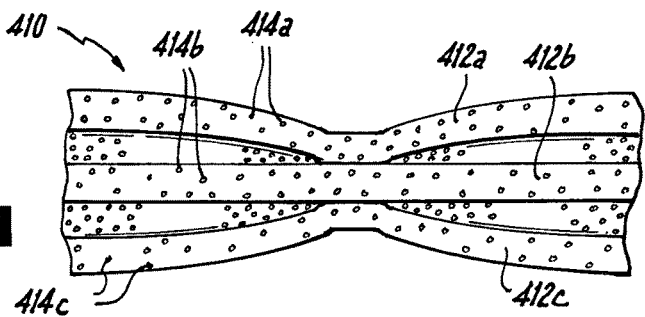
FIG. 5A is a partial, cross-sectional view of a surgical implant in accordance with another embodiment of the present disclosure.

FIG. 5A illustrates an embodiment of a surgical implant including varying degrees of porosity. Surgical implant 410 includes a first porous film layer 412a configured to be placed against an abdominal wall, a second porous film layer 412b, and a third porous film layer 412c configured to face the viscera. Each porous film layer 412a-412c includes openings 414a-414c, respectively. The first porous film layer 412a includes a relatively larger degree of porosity to encourage tissue ingrowth therein, while the third porous film layer 412c includes a relatively smaller degree of porosity to discourage tissue ingrowth and adhesion of tissue thereto. The second porous film layer 412b may include any degree of porosity.

Figure 5B:
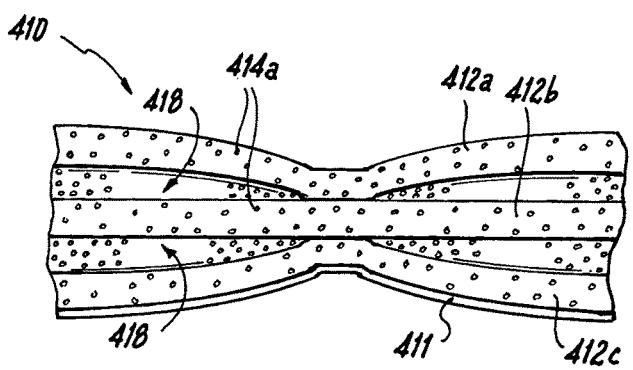
FIG. 5B is a partial, cross-sectional view of the surgical implant of FIG. 5A including an adhesion barrier in accordance with an embodiment of the present disclosure.

In embodiments, as illustrated in FIG. 5B, the third porous film layer 412c may be coated with a hydrophilic adhesion barrier layer 411 formed from a quick dissolving or rapidly bioerodible polymeric material so that any formed adhesion will detach from the surgical implant 410 once the adhesion barrier layer 411 dissolves. Examples of quick dissolving or rapidly bioerodible polymer materials include water soluble polymers such as poly(lactide-co-glycolide)s, polyanhydrides, polyorthoesters, polyvinyl alcohol, hydroxylpropyl methylcellulose, and carboxymethyl cellulose; biopolymers such as sugars, starches, salts, and gelatin; and derivatives and combinations thereof. In embodiments, the openings 414a and/or voids 418 of the surgical implant 410 may be loaded with filler materials (not shown) as described above. In any of the embodiments described herein, the implant can have voids that have different kinds of filler materials inside. E.g., a hemostat in one pocket and a cancer treating agent in another pocket. For example, one would fill the first pocket by capillary action, then dry the material, and then fill the second pocket with a different material.

Figure 6:
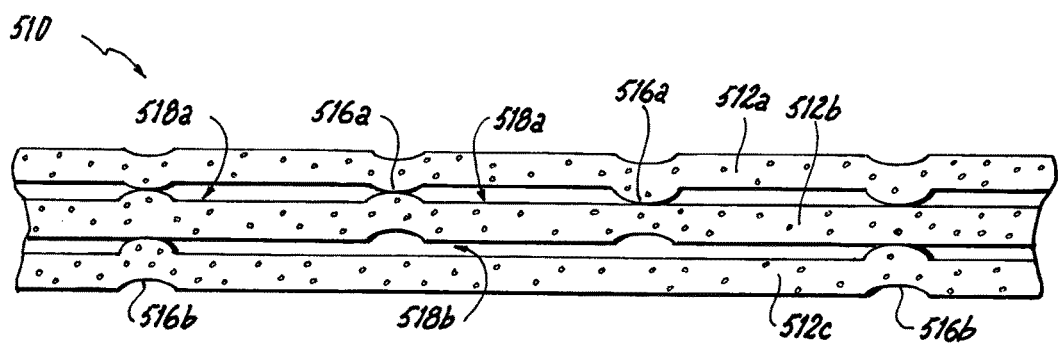
FIG. 6 is a partial, cross-sectional view of a surgical implant in accordance with yet still another embodiment of the present disclosure.

It should be understood that while the attachment points are shown as uniting all of the layers of a surgical implant at a common point, the attachment points may be distributed in a variety of patterns, such as only between two successive layers, between all stacked layers, and combinations thereof. As illustrated in FIG. 6, for example, surgical implant 510 includes first and second porous film layers 512a and 512b joined at attachment points 516a and including voids 518a therebetween. The third porous layer 512c is attached to the second porous layer 512b at spaced attachment points 516b joining all three layers 512a-512c along, for example, a periphery of the surgical implant 510, thereby creating, if desired, larger voids 518b between the second and third porous film layers 512b and 512c. The attachment points can be lines, dots, or have any shape.

Figure 7:
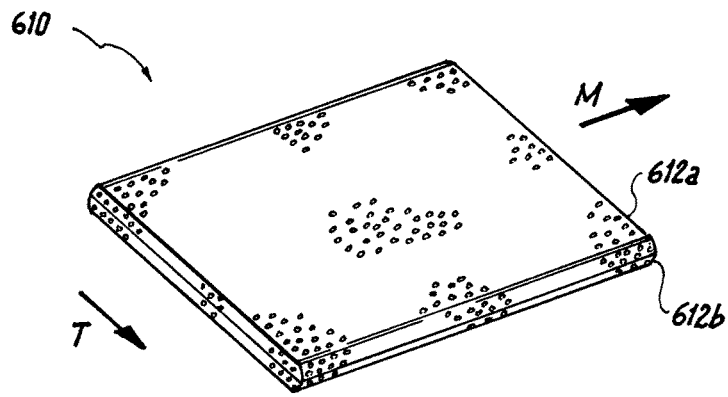
FIG. 7 is a perspective view of a surgical implant in accordance with another embodiment of the present disclosure.

Surgical implants in accordance with the present disclosure may also be utilized in reconstructive surgical procedures. As described above, mechanical properties of each porous layer, and thus the surgical implant, may be controlled by selecting, among other things, the materials, thickness, and pore density of each porous film layer. In embodiments, the production and assembly of the porous film layers may be tailored to provide improved size retention, toughness, and strength. The films may be drawn, stretched, molded or extruded under conditions, e.g., heated, ambient, or cooled temperatures in a machine and/or transverse direction, to produce films having different molecular orientation structures, and thus different film properties. The porous layers, each having different axial polymer chain alignments, may be stacked to produce a surgical implant having strong tensile properties in multiple planes. For example, FIG. 7 illustrates a surgical implant 610 including a first porous layer 612a having molecules uniaxially oriented in a machine direction "M", joined with a second porous layer 612b having molecules uniaxially oriented in a transverse direction "T". It should be understood that a surgical implant may also include biaxially-oriented films and/or films that have been incrementally stretched.

Figure 8:
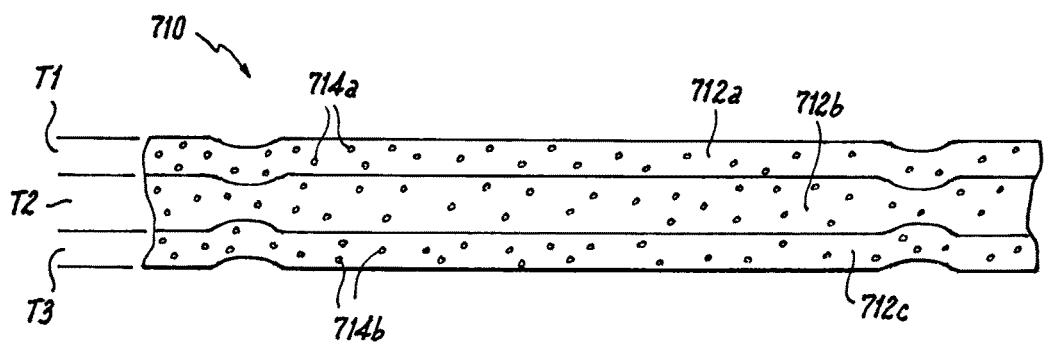
FIG. 8 is a cross-sectional view of a surgical implant in accordance with yet another embodiment of the present disclosure.

Surgical implants of the present disclosure may be utilized as scaffold materials for tissue regeneration. In embodiments, the porous layers of the surgical implant may be optimized for strength to support load bearing application and for cell attachment and ingrowth by providing a combination of porous layers of different thicknesses and surface areas. For example, FIG. 8 illustrates a surgical implant 710 including first and third porous film layers 712a and 712c of substantially the same thickness "T1" and "T3" disposed on opposing sides of a second porous film layer 712b having a thickness "T2", that is greater than thicknesses "T1" and "T3". Openings 714a and 714b provide the first and third porous film layers 712a and 712c with a textured surface with increased surface area for improved tissue integration.

In embodiments, the openings and/or voids may be loaded with filler materials, as discussed above. For example, the openings and/or voids may be loaded with adhesion protein or heparin sulfate conjugated hydrogels or charged beads, that recruit specific cell types and growth factors to encourage cellular ingrowth and maturation. The surgical implants may also be filled with growth factors or anti-inflammatory drugs to improve tissue regeneration.

Figure 9:
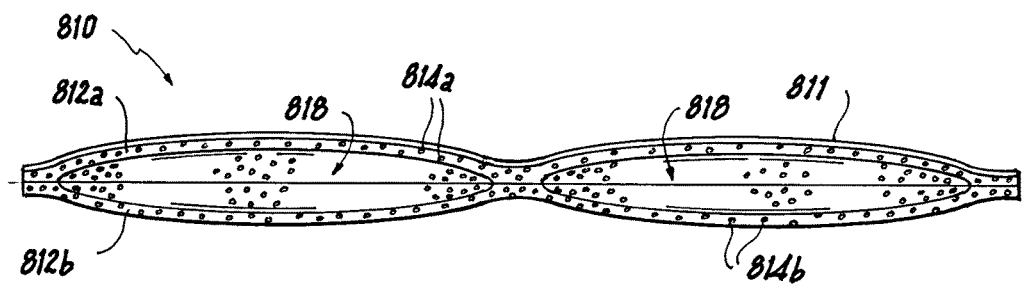
FIG. 9 is a cross-sectional view of a surgical implant in accordance with another embodiment of the present disclosure.

Surgical implants of the present disclosure may also be utilized for hemostasis. As illustrated in FIG. 9, a surgical implant 810 in the form of a hemostatic patch may include a first porous film layer 812a configured to face a wound and a second porous film layer 812b. The first porous film layer 812a may include an adhesive layer 811 to aid in the attachment of the surgical implant 810 to the wound. In embodiments, the adhesive layer may be a reactive adhesive material that includes functional groups for binding or attaching the surgical implant 810 to tissue by crosslinking with the reactive functional groups present in tissue, such as primary amine groups, secondary amine groups, hydroxyl groups, carboxylic groups, sulfonic groups, combinations thereof, and the like. In embodiments, the reactive adhesive layer 811 may be an in situ polymerizable hydrogel, e.g., commercially available products such as FOCALSEAL® (Genzyme, Inc.), COSEAL® (Angiotech Pharmaceuticals), and DURASEAL® (Confluent Surgical, Inc).

While the first porous film layer 812a includes a sufficient number of openings 814a to allow for blood to infiltrate the surgical implant 810, such as through capillary or microfluidic filling, the second porous film layer 812b includes a minimal number and size of openings 814b to allow for the transfer of gases while encouraging blood retention in the surgical implant 810. In embodiments, absorbent materials could be included in the openings 814a, 814b and/or voids 818 of the surgical implant 810. Absorbent materials, e.g., hydrogels, allow collected blood and other wound fluid to gel and/or solidify thereby consolidating and containing these fluids in the surgical implant 810. Absorbent materials may swell during blood absorption, thereby exerting pressure on the wound to further reduce bleeding.

Surgical implants of the present disclosure may be utilized as a sealant or tissue patch, for example in duraplasty or lung sealant applications. As discussed with respect to FIG. 9 above, a first porous film layer 812a may include an adhesive material 811 for attachment to tissue, and a second porous film layer 812b may include a minimal number of openings 814b to provide a liquid sealed barrier. The porous film layers 812a and 812b would allow fluid filling or tissue ingrowth over time thereby encouraging integration into surrounding tissue.

In embodiments, a surgical implant may be fabricated with porous film layers that match the elastic behavior of the tissue in which the surgical implant is placed. For example, in a lung sealing application, the porous film layers of a surgical implant may be formed of elastomeric degradable polymeric materials, such as polyurethanes, to substantially match lung elasticity and to be distensible during lung inflation and retraction during breathing.

In any of the embodiments disclosed herein, the film material can be a combination of biodegradable materials, a combination of non-degradable materials, or a combination thereof. In at least certain embodiments, it is preferred that both layers are made from biodegradable materials. It is contemplated that each of the first porous film layer and second porous film layers are both fabricated from at least one biodegradable material, from different biodegradable materials, from one biodegradable material and one non-biodegradable, or from at least two non-biodegradable materials.

While the above description contains many specifics, these specifics should not be construed as limitations on the scope of the present disclosure, but merely as exemplifications of embodiments thereof. It will be understood that various modifications may be made to the embodiments disclosed herein. Therefore, the above description should not be construed as limiting, but merely as exemplifications within the scope and spirit of the claims of the present disclosure.

What is claimed is:

1. A surgical stapling apparatus comprising:
a handle assembly;
a tubular body portion extending from the handle assembly;
a staple cartridge assembly extending from the tubular body portion;
an anvil assembly coupled to the staple cartridge assembly and movable relative thereto between open and closed positions; and
a surgical buttress releasably attached to the staple cartridge assembly or the anvil assembly, the surgical buttress including first, second, and third porous film layers successively stacked on each other and interconnected at a plurality of attachment points that define a plurality of pockets between the first and second porous film layers and the second and third porous film layers, wherein the plurality of attachment points between the first and second porous film layers of the surgical buttress are different from the plurality of attachment points between the second and third porous film layers of the surgical buttress such that the plurality of attachment points form at least one of the plurality of pockets between the first and second porous film layers that is different in size from at least one of the plurality of pockets between the second and third porous film layers.

2. The surgical stapling apparatus of claim 1, wherein the first and second porous film layers of the surgical buttress are substantially planar.

3. The surgical stapling apparatus of claim 1, wherein the surgical buttress includes a filler material disposed within at least one of the plurality of pockets defined between the first and second porous film layers.

4. The surgical stapling apparatus of claim 3, wherein the filler material is a drug.

5. The surgical stapling apparatus of claim 3, wherein the filler material is a hydrogel.

6. The surgical stapling apparatus of claim 3, wherein the filler material is an adhesive.

7. The surgical stapling apparatus of claim 1, wherein the first and second porous film layers of the surgical buttress are bonded together at the plurality of attachment points.

8. The surgical stapling apparatus of claim 1, wherein the first porous film layer of the surgical buttress has a first thickness and the second porous film layer of the surgical buttress has a second thickness that is different from the first thickness.

9. The surgical stapling apparatus of claim 1, wherein the first porous film layer of the surgical buttress has a first modulus of elasticity and the second porous film layer of the surgical buttress has a second modulus of elasticity that is different from the first modulus of elasticity.

10. The surgical stapling apparatus of claim 1, wherein the first porous film layer of the surgical buttress has a first degree of porosity and the second porous film layer of the surgical buttress has a second degree of porosity that is different form the first degree of porosity.

11. The surgical stapling apparatus of claim 1, wherein the surgical buttress further includes an adhesive layer applied to an outer surface of the first porous film layer.

12. The surgical stapling apparatus of claim 1, wherein the surgical buttress includes a central aperture defined therethrough.

13. The surgical stapling apparatus of claim 12, wherein the anvil assembly includes an anvil member and a shaft, the surgical buttress positionable on the shaft of the anvil assembly.

14. The surgical stapling apparatus of claim 1, wherein each of the first and third porous film layers of the surgical buttress has a first thickness and the second porous film layer of the surgical buttress has a second thickness that is greater than the first thickness.

15. The surgical stapling apparatus of claim 1, wherein the second porous film layer of the surgical buttress is fabricated from a material having a higher modulus of elasticity than materials of the first and third porous film layers of the surgical buttress.

* * * * *